(12) United States Patent
Alkhatib

(10) Patent No.: US 10,271,947 B2
(45) Date of Patent: Apr. 30, 2019

(54) HEART VALVE CHORDAE REPLACEMENT METHODS AND APPARATUS

(71) Applicant: St. Jude Medical, LLC, Abbott Park, IL (US)

(72) Inventor: Yousef F. Alkhatib, Edina, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 718 days.

(21) Appl. No.: 13/623,304

(22) Filed: Sep. 20, 2012

(65) Prior Publication Data

US 2013/0253639 A1 Sep. 26, 2013

Related U.S. Application Data

(62) Division of application No. 12/074,586, filed on Mar. 4, 2008, now Pat. No. 8,303,622.
(Continued)

(51) Int. Cl.
*A61F 2/24* (2006.01)
*A61B 17/04* (2006.01)
(Continued)

(52) U.S. Cl.
CPC ........ *A61F 2/2427* (2013.01); *A61B 17/0401* (2013.01); *A61F 2/2442* (2013.01);
(Continued)

(58) Field of Classification Search
CPC .. A61B 2017/22098; A61B 2017/3486; A61B 2017/22048; A61B 2017/22051; A61B 2017/22069; A61B 5/68; A61B 5/6843; A61B 5/6844; A61B 5/6885; A61B 5/6886; A61B 2562/0247; A61B 2562/0257; A61B 2562/04–2562/046;
(Continued)

(56) References Cited

U.S. PATENT DOCUMENTS 2,623,521 A 12/1952 Shaw
3,515,139 A * 6/1970 Mallina ................ A61B 17/282
606/207
(Continued)

FOREIGN PATENT DOCUMENTS

WO 2006078694 A3 4/2009

*Primary Examiner* — Ryan J. Severson
*Assistant Examiner* — Charles M Wei
(74) *Attorney, Agent, or Firm* — Lerner, David, Littenberg, Krumholz & Mentlik, LLP

(57) ABSTRACT

Apparatus for attaching a prosthetic tether between a leaflet of a patient's heart valve and another portion of the patient's heart to help prevent prolapse of the leaflet and/or to otherwise improve leaflet function. The apparatus can be used with relatively low invasiveness of the patient's body. The apparatus releasably clamps the leaflet during attachment of the tether to the leaflet. The apparatus may include an integrated display for indicating how extensively the leaflet is being clamped, as well as structure for stabilizing the leaflet for better clamping. The apparatus may enter the heart through an aperture in the wall of the heart, and may include structure for helping to reduce blood leakage from that aperture. The apparatus may be able to enter the heart by following a guide wire. The apparatus may include various means for attaching the tether to the leaflet.

10 Claims, 20 Drawing Sheets

Related U.S. Application Data

(60) Provisional application No. 60/918,183, filed on Mar. 14, 2007.

(51) Int. Cl.
    *A61B 17/064*     (2006.01)
    *A61B 17/08*     (2006.01)
    *A61B 17/00*     (2006.01)
    *A61B 17/06*     (2006.01)
    *A61B 18/00*     (2006.01)
    *A61B 90/00*     (2016.01)

(52) U.S. Cl.
    CPC .......... *A61F 2/2457* (2013.01); *A61B 17/064* (2013.01); *A61B 17/08* (2013.01); *A61B 2017/00247* (2013.01); *A61B 2017/00867* (2013.01); *A61B 2017/0417* (2013.01); *A61B 2017/0649* (2013.01); *A61B 2017/06052* (2013.01); *A61B 2018/00392* (2013.01); *A61B 2090/036* (2016.02)

(58) Field of Classification Search
    CPC .................. A61F 2/2457; A61F 2/2427; A61F 2017/22069
    USPC ............................. 606/1, 221, 144, 205–211
    See application file for complete search history.

(56) References Cited

U.S. PATENT DOCUMENTS

| | | | |
|---|---|---|---|
| 4,258,716 A * | 3/1981 | Sutherland | A61B 17/320016 606/170 |
| 4,535,773 A | 8/1985 | Yoon | |
| 5,261,891 A | 11/1993 | Brinkerhoff et al. | |
| 5,295,958 A * | 3/1994 | Shturman | 604/103.07 |
| 5,339,799 A | 8/1994 | Kami et al. | |
| 5,454,819 A * | 10/1995 | Knoepfler | A61B 17/062 606/147 |
| 5,470,316 A | 11/1995 | Tovey et al. | |
| 5,609,607 A | 3/1997 | Hechtenberg et al. | |
| 5,706,998 A | 1/1998 | Plyley et al. | |
| 5,713,368 A | 2/1998 | Leigh | |
| 6,079,414 A * | 6/2000 | Roth | 128/898 |
| 6,419,626 B1 * | 7/2002 | Yoon | A61B 1/00052 600/103 |
| 6,752,813 B2 * | 6/2004 | Goldfarb | A61B 17/12 606/139 |
| 7,112,207 B2 * | 9/2006 | Allen | A61B 17/0401 128/898 |
| 7,635,386 B1 * | 12/2009 | Gammie | A61B 17/0469 623/2.11 |
| 7,717,312 B2 | 5/2010 | Beetel | |
| 7,866,526 B2 | 1/2011 | Green et al. | |
| 7,975,894 B2 | 7/2011 | Boyden et al. | |
| 8,052,592 B2 * | 11/2011 | Goldfarb | A61B 17/0401 600/37 |
| 8,579,177 B2 * | 11/2013 | Beetel | A61B 17/068 227/175.1 |
| 2002/0183738 A1 | 12/2002 | Chee et al. | |
| 2003/0032950 A1 | 2/2003 | Altshuler et al. | |
| 2003/0105474 A1 * | 6/2003 | Bonutti | A61B 17/04 606/139 |
| 2003/0120264 A1 * | 6/2003 | Lattouf | 606/1 |
| 2004/0176754 A1 * | 9/2004 | Island | A61B 18/203 606/9 |
| 2005/0267453 A1 * | 12/2005 | Wong et al. | 606/27 |
| 2006/0273135 A1 | 12/2006 | Beetel | |
| 2007/0038206 A1 * | 2/2007 | Altshuler | A46B 15/0036 606/20 |
| 2007/0299468 A1 * | 12/2007 | Viola | A61B 5/0084 606/205 |
| 2008/0188873 A1 * | 8/2008 | Speziali | A61B 17/0469 606/144 |
| 2008/0294153 A1 | 11/2008 | Altshuler et al. | |
| 2010/0036379 A1 * | 2/2010 | Prakash | A61B 5/053 606/51 |
| 2010/0152586 A1 * | 6/2010 | Grant | A61B 5/489 600/454 |

* cited by examiner

HEART VALVE CHORDAE REPLACEMENT METHODS AND APPARATUS

CROSS-REFERENCE TO RELATED APPLICATIONS

This application is a divisional application of U.S. application Ser. No. 12/074,586, filed Mar. 4, 2008, which claims the benefit of U.S. Provisional Patent Application No. 60/918,183, filed Mar. 14, 2007, the disclosures of which are hereby incorporated by reference herein.

BACKGROUND OF THE INVENTION

This invention relates to methods and apparatus for improving the functioning of a patient's heart, and more particularly to improving the functioning of a patient's mitral or tricuspid valve by adding at least one chordal attachment from at least one leaflet of the valve to the wall of the associated ventricle.

International patent application publication WO 2006/078694 A2, entitled "Thorascopic Heart Valve Repair Method and Apparatus" ("the '694 reference"), shows methods and apparatus for repairing a heart valve, e.g., by entering the heart thorascopically through the apex of the heart. The thorascopic instrument is used to engage a leaflet of a heart valve (e.g., the mitral valve) and to pass a suture through the leaflet. The instrument is then retracted from the heart, and the suture (which is still attached to the leaflet) is anchored to the wall of the heart. The suture, which thus now extends from the leaflet to the wall of the heart, acts as a chorda-like attachment or tether, replacing native ruptured or elongated chordae. This can help improve performance of the valve, e.g., by reducing or eliminating leaflet prolapsing and/or by improving coaptation of the leaflets when, during its operating cycle, the valve is supposed to optimally open and close.

An objective of the '694 reference is to perform the heart repair shown without stopping the patient's heart and by means that are less invasive than a full sternotomy and an open heart. By performing the procedure on a beating heart, an objective can be to adjust the length of the replacement suture or tether during the procedure to achieve the best valve performance. The '694 reference employs additional external equipment for functioning (e.g., external light sources, external power sources, external monitor display, external camera and camera coupler, external fiber optic strands extending beyond the instrument handle, etc.).

There are various respects in which it may be possible to improve on what is shown in the '694 reference.

SUMMARY OF THE INVENTION

In accordance with certain embodiments of the invention, apparatus for attaching a tether (i.e., an artificial prosthetic chorda) between a leaflet of a patient's heart valve and another portion of the heart may include an elongated shaft having a proximal end and a distal end; first and second jaw surfaces near the distal end of the shaft, the jaw surfaces being movable relative to one another to admit tissue of the leaflet between the jaw surfaces and to releasably clamp the tissue between the jaw surfaces; and a leaflet stabilization structure deployable from the shaft distal of the jaw surfaces for at least partly restraining movement of the leaflet. The leaflet stabilization structure may include a resiliently expandable wire mesh structure. Alternatively, the leaflet stabilization structure may include an inflatable balloon.

The shaft may include a lumen extending along a longitudinal axis of the shaft from the proximal end to the distal end. In such embodiments, the apparatus may further include a control mechanism disposed in the lumen and operable to control deployment of the leaflet stabilization structure. The control mechanism may be operable to control retraction of the leaflet stabilization structure.

The leaflet stabilization structure may be deployable from an aperture in the distal end of the shaft. The shaft may include a lumen extending along a longitudinal axis of the shaft from the proximal end to the distal end, and the aperture may be the distal end of the lumen.

In accordance with other embodiments of the invention, apparatus for attaching a tether between a leaflet of a patient's heart valve and another portion of the heart may include an elongated shaft insertable through an aperture in the wall of the patient's heart, the shaft having a proximal end and a distal end; first and second jaw surfaces near the distal end of the shaft, the jaw surfaces being movable relative to one another to admit tissue of the leaflet between the jaw surfaces and to releasably clamp the tissue between the jaw surfaces; and an annular sealing structure disposed concentrically around the shaft proximally of the jaw surfaces for resiliently bearing against an outer surface of the wall of the heart annularly around the aperture when the shaft is inserted through the aperture to reduce blood leakage through the aperture.

The sealing structure may be slidable along the length of the shaft, and may be resiliently biased to slide in a distal direction along the length of the shaft.

In accordance with further embodiments of the invention, apparatus for attaching a tether between a leaflet of a patient's heart valve and another portion of the heart may include an elongated shaft having a proximal end and a distal end; first and second jaw surfaces near the distal end of the shaft, the jaw surfaces being movable relative to one another to admit tissue of the leaflet between the jaw surfaces and to releasably clamp the tissue between the jaw surfaces; and a lumen extending through the shaft from the proximal end to a point distal of the jaw surfaces, the lumen being sized to receive a guide wire. The lumen may extend through the shaft.

In accordance with yet further embodiments of the invention, apparatus for attaching a tether between a leaflet of a patient's heart valve and another portion of the heart may include an elongated shaft having a proximal end and a distal end; first and second jaw surfaces near the distal end of the shaft, the jaw surfaces being movable relative to one another to admit tissue of the leaflet between the jaw surfaces and to releasably clamp the tissue between the jaw surfaces; an elongated, laterally flexible needle insertable longitudinally into and along the shaft; and a tether attached to the needle. The shaft may be configured to guide the needle distally past the jaw surfaces and then back proximally past the jaw surfaces, the needle passing at least once through tissue clamped between the jaw surfaces as it passes the jaw surfaces in order to pull the tether through the tissue.

In still further embodiments of the invention, apparatus for attaching a tether between a leaflet of a patient's heart valve and another portion of the heart may include an elongated shaft having a proximal end and a distal end; first and second jaw surfaces near the distal end of the shaft, the jaw surfaces being movable relative to one another to admit tissue of the leaflet between the jaw surfaces and to releasably clamp the tissue between the jaw surfaces; a resiliently expandable tissue anchor disposed in the shaft adjacent one of the jaw surfaces; a tether attached to the tissue anchor;

and means for driving the tissue anchor through tissue clamped between the jaw surfaces.

In yet other embodiments of the invention, apparatus for attaching a tether between a leaflet of a patient's heart valve and another portion of the heart may include an elongated shaft having a proximal end and a distal end, and a lumen extending along a longitudinal axis of the shaft; first and second jaw surfaces near the distal end of the shaft, the jaw surfaces being movable relative to one another to admit tissue of the leaflet between the jaw surfaces and to releasably clamp the tissue between the jaw surfaces; a tissue clip disposed in a substantially straight configuration in the lumen of the shaft, the clip being deformable from the substantially straight configuration to a coiled configuration; a tether attached to the clip; and means for pushing the clip distally from the lumen through tissue clamped between the jaw surfaces, whereupon the clip deforms to the coiled configuration and thereby clips onto the tissue.

In accordance with still further embodiments of the invention, apparatus for attaching a tether between a leaflet of a patient's heart valve and another portion of the patient's heart may include an elongated shaft having a proximal end and a distal end; first and second jaw surfaces near the distal end of the shaft, the jaw surfaces being movable relative to one another to admit tissue of the leaflet between the jaw surfaces and to releasably clamp the tissue between the jaw surfaces; and a deformable tissue clip having first and second arms respectively adjacent the first and second jaw surfaces, the arms being movable from a spaced apart condition for admitting the tissue between the arms to a clamping condition for clamping the tissue between the arms. The arms may be resiliently biased to move from the spaced apart condition to the clamping condition. Each of the arms may be releasably secured to one of the jaw surfaces.

In accordance with another aspect of the invention, apparatus for temporarily reducing motion of at least one leaflet in a heart valve in a patient's beating heart may include an elongated structure insertable into the patient to a location adjacent the heart valve. The elongated structure may include a leaflet stabilization structure deployable into contact with the at least one leaflet. The leaflet stabilization structure may include a mesh of wires resiliently biased to expand into contact with the at least one leaflet when deployed to apply mechanical pressure to the at least one leaflet while allowing blood to flow through the mesh.

The heart valve may include at least two leaflets, and the mesh of wires may be deployable between the at least two leaflets. The mesh of wires may be resiliently expandable to push the at least two leaflets apart while allowing blood to flow through the valve through the mesh of wires. The mesh of wires may be collapsible for removal from the patient.

Further features of the invention, its nature and various advantages, will be more apparent from the accompanying drawings and the following detailed description.

BRIEF DESCRIPTION OF THE DRAWINGS

FIG. 10 shows possible additional details, some of which are internal to other structure but which are shown as though visible through that other structure.

DETAILED DESCRIPTION

Figure 1:
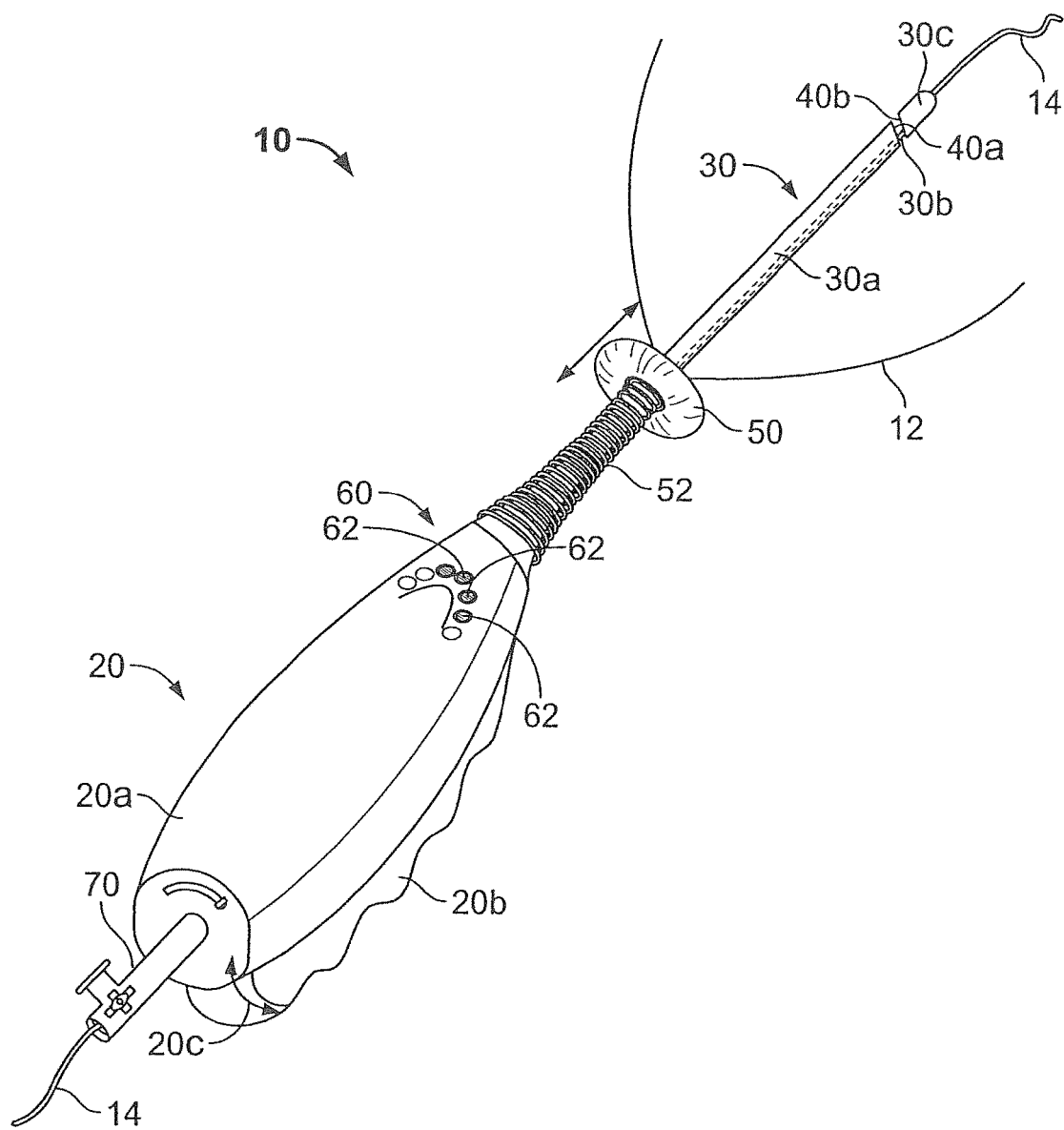
FIG. 1 is a simplified isometric or perspective view of an illustrative embodiment of apparatus in accordance with the invention.

An illustrative embodiment of heart valve leaflet tether (or artificial prosthetic chorda) attaching apparatus 10 in accordance with the present invention is shown in FIG. 1. Apparatus 10 includes a handle portion 20 and an elongated shaft portion 30. Handle portion 20 is designed to remain outside the patient's body at all times so that it can be held in a hand of the operator (e.g., a surgeon) and directly viewed by the operator while in the operator's hand. Shaft portion 30 is designed for axial (i.e., in a direction along its longitudinal axis) insertion into the patient with relatively low invasiveness of the patient's body. For example, shaft 30 may be inserted through a relatively small incision in the patient's chest, between two of the patient's ribs, and then through the apex of the patient's heart to extend up through the left or right ventricle to the patient's heart valve to be repaired (mitral valve in the case of the left ventricle; tricuspid valve in the case of the right ventricle). FIG. 1 shows the outline of a portion of the patient's heart 12 near the apex with shaft 30 passing through the apex and into one of the ventricles of the heart.

FIG. 1 illustrates the possibility that apparatus 10 may be introduced into the patient "over" (i.e., along) a guide wire 14 that was previously introduced in the patient via other apparatus, which other apparatus can be even more slender than shaft 30 where it enters the patient. For this purpose, apparatus 10 may have a guide wire lumen that passes along its interior between a distal aperture at the distal end of shaft 30 and a proximal aperture in handle portion 20.

A distal portion of shaft 30 has two jaw surfaces 40a and 40b. In the FIG. 1 embodiment, jaw surfaces are transverse to the longitudinal axis of shaft 30 (i.e., they are inclined relative to the longitudinal axis of the shaft). The angle of incline shown in FIG. 1 is only illustrative, and other angles can be used instead if desired.

Jaw surfaces 40a and 40b are movable toward and away from one another along the longitudinal axis of shaft 30. This is done by moving a distal-most portion 30c of shaft 30 (of which jaw surface 40b is the proximal end or face) toward or away from jaw surface 40a parallel to the longitudinal axis of shaft 30. For this purpose, distal-most portion 30c is supported on one or more longitudinal supports 30b that movably extend from more proximal shaft portion 30a. Supports 30b are much closer to one side of shaft portions 30a and 30c than to the other side of those shaft portions. In particular, in the orientation shown in FIG. 1, supports 30b are closer to the lower side of shaft portions 30a and 30c. This leaves the upper space between jaw surfaces 40a and 40b open when the jaw surfaces are moved apart as shown in FIG. 1. An edge portion of a leaflet of the patient's mitral or tricuspid valve can be received in this open (upper) space between jaw surfaces 40a and 40b when those surfaces are thus open. When such leaflet tissue is between the jaws, jaw surfaces 40a and 40b can be moved back toward one another to releasably clamp that tissue between the jaws.

The movable supports 30b for movable distal shaft portion 30c and distal jaw surface 40b are linked (inside proximal shaft portion 30a) to a movable portion 20b of handle 20. In particular, movable handle portion 20b can be squeezed toward stationary handle portion 20a to cause elements 30b, 30c, and 40b to move proximally toward or distally away from elements 30a and 40a. Bi-directional, arcuate arrow 20c indicates how movable portion 20b may be pivoted toward or away from stationary portion 20a. For example, the pivot point for this relative motion may be near the distal end of handle 20. Handle portions 20a and 20b may be resiliently biased to pivot apart, with squeezing by a hand of the operator being required to pivot parts 20a and 20b toward one another. The linkage between handle 20 and the distal portions of shaft 30 may be such that jaws 40a and 40b are closed (i.e., closest to one another) when there is no manual squeezing pressure on handle portions 20a and 20b, and such that squeezing handle portion 20b toward handle portion 20a causes distal elements 30b, 30c, and 40b to move distally away from more proximal elements 30a and 40a. In such an embodiment, the resilient opening bias between handle portions 20a and 20b produces a resilient closing or clamping bias between jaw surfaces 40a and 40b. Thus, when leaflet tissue is interposed between open jaws 40a and 40b, and the squeezing pressure on handle portions 20a and 20b is released, jaws 40a and 40b automatically close on and apply resilient clamping pressure to the leaflet tissue between the jaws.

If desired, the above-described linkage between handle 20 and jaws 40a and 40b can be reversed so that the jaws are open when the handle is not being squeezed, and so that squeezing of the handle is required to close the jaws and clamp leaflet tissue between the jaws. In such an embodiment, a releasable latch can be added to the handle structure to maintain the handle in a squeezed condition (and jaws 40 in a closed, tissue-clamping condition) even when no squeezing pressure is being applied to the handle.

A possible feature of the invention that is illustrated by FIG. 1 is a donut balloon or grommet 50 around a proximal portion of shaft 30 for helping to seal the aperture through the apex of heart 12 via which the more distal portion of shaft 30 enters the heart. Donut 50 extends annularly around shaft 30. It fits relatively closely around the shaft, but it is nevertheless axially movable along the length of the shaft. Donut 50 is resiliently urged to move in the distal direction along shaft 30 by a spring 52 that is coiled around a more proximal portion of shaft 30. In particular, as shaft 30 is inserted into the patient's heart, donut 50 contacts the apex of heart 12 around the aperture through which shaft 30 is entering the heart. Continued distal motion of shaft 30 into heart 12 causes donut 50 to move proximally back along shaft 30, while accumulating compression of spring 52 keeps donut 50 pressed against the outer surface of the heart around the entry aperture. This pressure of donut 50 on the heart helps to reduce blood leakage from the heart via the aperture in the heart around shaft 30.

Another possible feature of the invention that is illustrated by FIG. 1 is visual display 60 that is integrated into handle 20, preferably where the display is always readily visible to the operator of the apparatus. As will be described in more detail later, display 60 indicates the extent to which leaflet tissue has been captured between jaws 40. This may be done with an arrangement of a plurality of lights 62 that approximates the available space between jaws 40, with each of lights 62 corresponding to a respective portion of that space and indicating (e.g., by its color or by whether it is on or off) whether tissue is present in the associated portion of the space between the jaws. In the illustrative embodiment shown in FIG. 1, display 60 is disposed on the side of handle 20 that is generally toward the face (and therefore the eyes) of the operator of the apparatus. In addition, display 60 is preferably distal of the portion of the handle that the operator covers with his or her hand during use of the apparatus (e.g., to insert shaft 30 into the patient and to move jaws 40 relative to one another). In this way, display 60 is preferably visible to the operator at all times during which the operator may wish to see it, and even while the operator is squeezing handle 20 to open and/or close jaws 40 to accept and clamp tissue between the jaws.

Display 60 may require electrical circuitry and electrical power for its operation. If so, that electrical circuitry and an electrical power source (e.g., a battery) are preferably integrated into apparatus 10. For example, the larger portions of such components may be built into handle 20. An electrical on/off switch is shown on the proximal end of handle 20 for turning these electrical components (and thus display 60) on or off.

A final component that is illustrated by FIG. 1 is structure 70, which can have any of a wide range of constructions, and which can serve any of a wide range of purposes. For example, structure 70 can include a proximal port for guide wire 14. Alternatively or in addition, structure 70 can provide a proximal port for an optional balloon or other distally deployable structure for stabilizing a leaflet to be grasped between jaws 40. As still another example, structure 70 can alternatively or additionally provide a proximal port for introduction and/or control of the elements that attach a tether to the leaflet tissue that is clamped between jaws 40. Thus, structure 70 provides one or a plurality of ports, each of which is connected to a respective lumen that passes through handle structure 20 into elongated shaft structure 30. Each of these lumens passes longitudinally through at least a portion of the length of shaft structure 30 (e.g., to where the lumen needs to exit at or near the distal end of the shaft structure, depending on how that lumen is configured to be used). For example, such a port and the respective lumen may be configured for any one or more of a number of possible uses (e.g., introducing a fluid into the patient, introducing a wire (e.g., a guide wire like 14) into the patient, introducing a needle into the patient, removing such a needle from the patient (e.g., after the needle has curved back and thereby reversed direction inside the patient), introducing a length of suture into the patient, introducing a temporary leaflet stabilization structure into the patient (e.g., as in FIGS. 4-9), etc.). (The above reference to the needle curving back and reversing direction is typically the result of the needle being guided by the apparatus to pass from a first, in-bound needle lumen in the apparatus to a second, different, out-bound needle lumen in the apparatus. More regarding this type of structure will be shown and described later in this specification (e.g., in connection with FIG. 22).)

Figure 2:
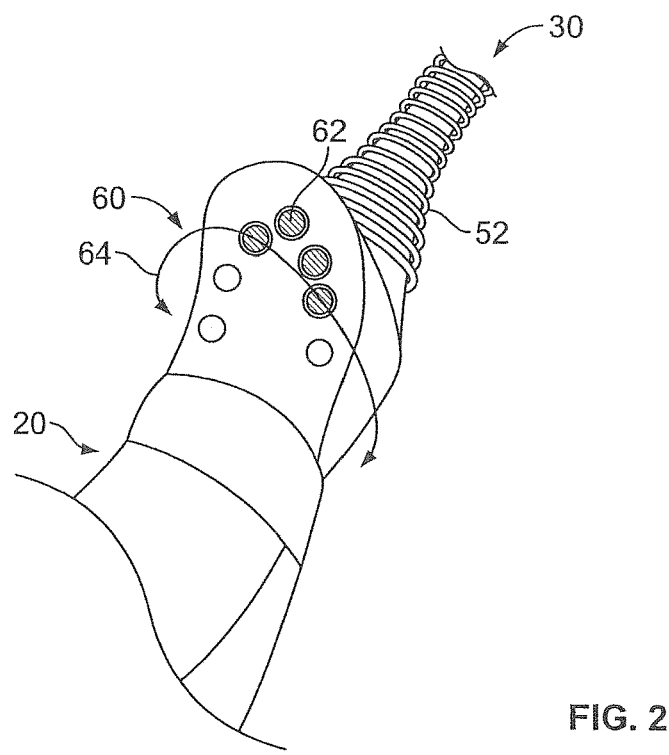
FIG. 2 is similar to a portion of FIG. 1 for another illustrative embodiment of the invention.

FIG. 2 shows another illustrative embodiment in which display 60 is on a portion of handle 20 that is rotatable about a longitudinal axis of the apparatus. This rotatability of display 60 is indicated by the double-headed arcuate arrow 64 in FIG. 2. Such rotatability of display 60 can help the operator of the apparatus keep the display visible, even if the operator finds it necessary to rotate the remainder of the apparatus so that the display would otherwise be out of the operator's convenient line of sight. Note that in FIG. 2 display 60 is still preferably distal of the portion of handle 20 that the operator typically covers with a hand during use.

Figure 3:
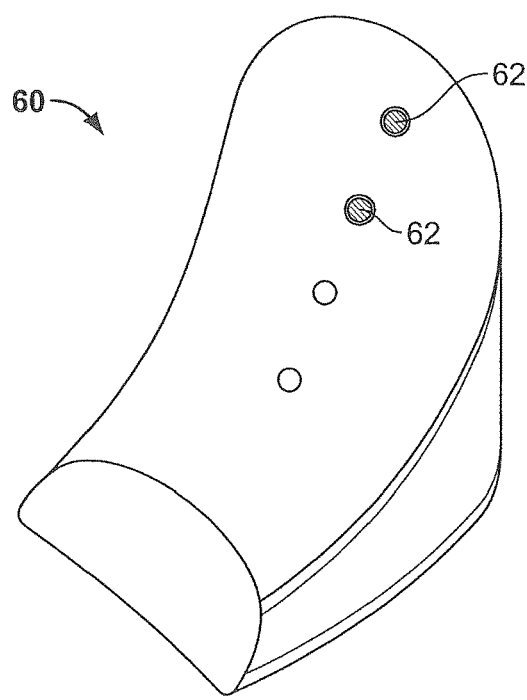
FIG. 3 is again similar to a portion of FIG. 1 for still another illustrative embodiment of the invention.
Figure 4:
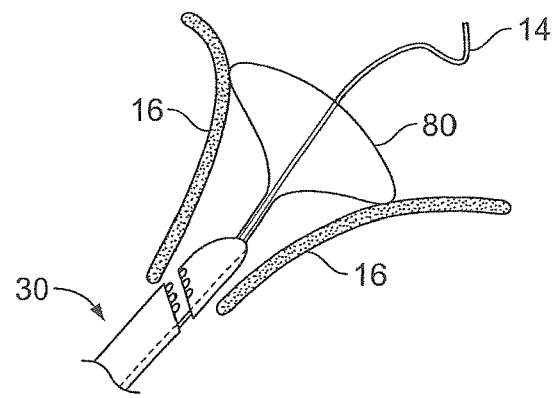
FIGS. 4-9 are similar to a portion of FIG. 1 for several alternative embodiments of a possible additional feature in accordance with the invention.
Figure 5:
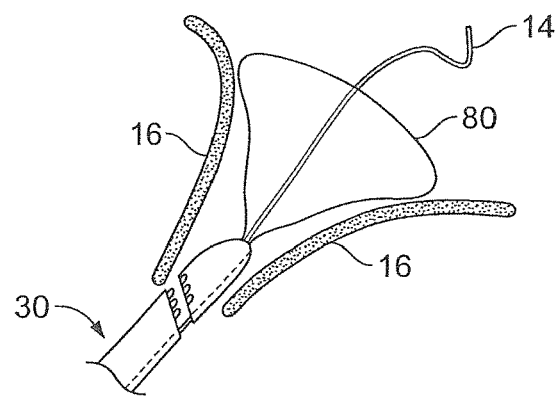
Figure 6:
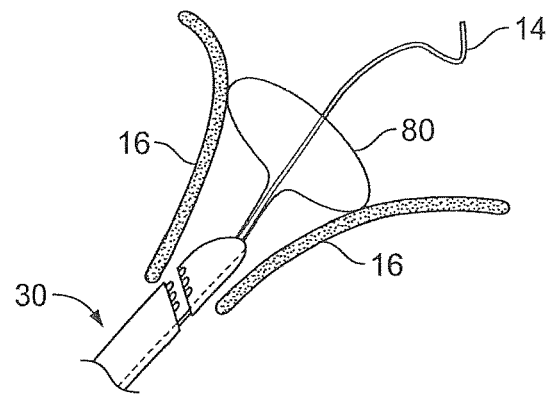
Figure 7:
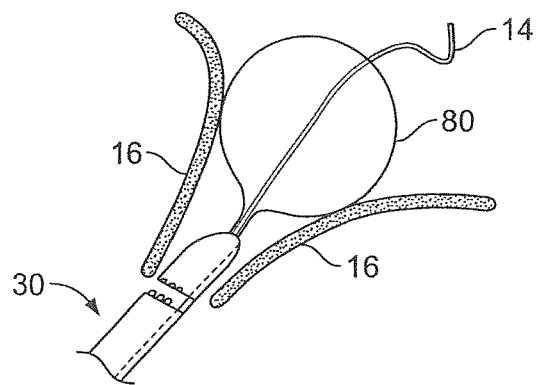
Figure 8:
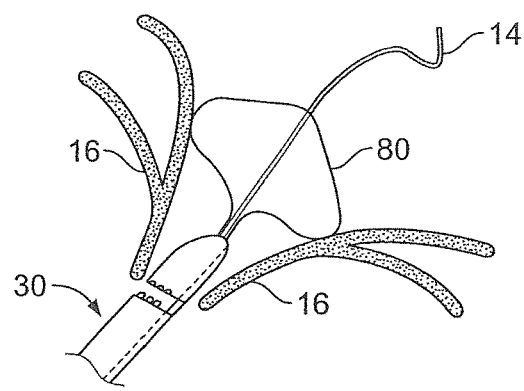

FIG. 3 illustrates an alternative configuration of the indicators (e.g., lights) 62 of display 60. In this alternative, lights 62 are in a straight line that is representative of the possible depth of penetration of the space between jaws 40 by the patient's heart valve leaflet tissue. In other words, each of lights 62 is associated with a respective different amount of penetration of the inter-jaw space by leaflet tissue (e.g., distal-most light 62 indicating shallowest penetration, and each more proximal light 62 indicating greater and greater penetration). Whereas the displays 60 in FIGS. 1 and 2 attempt to indicate where around the inter-jaw space tissue is present, the FIG. 3 display attempts to indicate the depth of tissue penetration into the inter-jaw space. The FIG. 3 display may be rotatable about a longitudinal axis of the apparatus (like the FIG. 2 display).

FIGS. 4-9 show various illustrative embodiments of structures that can be deployed from a distal end of apparatus to stabilize at least one of the patient's heart valve leaflets for easier and better capture between the jaws 40 of the apparatus. In FIGS. 4-8 the leaflet stabilization structure comprises an inflatable/deflatable balloon 80. FIGS. 4-8 show that such a balloon 80 can be preformed to have any of a wide range of shapes. The balloon 80 may be deployed concentrically around guide wire 14 and via the same lumen through apparatus 10 as is used for the guide wire. Alternatively, balloon 80 may be deployed from another lumen through apparatus 10. When balloon 80 is deployed, it bears on at least one of the patient's heart valve leaflets 16. This helps to reduce the natural motion of the leaflet, which makes it easier for apparatus 10 to capture the leaflet between jaws 40. After a leaflet 16 has been captured between the instrument's jaws, balloon 80 can be deflated and withdrawn. (If still present at this time, guide wire 14 is also typically withdrawn after a leaflet has been captured between the instrument's jaws.)

Figure 9:
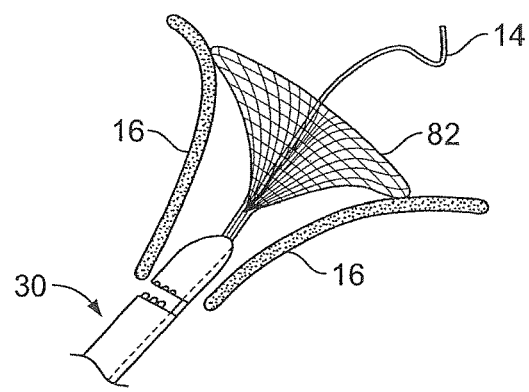

FIG. 9 shows the alternative of using a braided wire basket 82 (instead of a balloon 80) for leaflet stabilization. For example, basket 82 may be formed from a braid of fine nitinol wires that is resiliently biased to expand to the size and shape shown in FIG. 9 when released from confinement within a lumen of apparatus 10. After basket 82 has performed its leaflet stabilization task, it can be pulled back into its deployment lumen and withdrawn. As in the case of the various illustrative shapes depicted for balloon 80 in FIGS. 4-8, the shape shown for basket 82 in FIG. 9 is only an example, and any of a wide range of other shapes can be used.

In general, FIGS. 4-9 illustrate the principle that device 10 can have one or more longitudinal channels or lumens through it that can be used for ancillary and support procedural devices (e.g., balloon catheters, braided wire baskets, saline fluid, flushing contrast solution for visualization, etc.) The device 10 itself can be advanced over a guide wire 14 if needed. Alternatively, it can be advanced without a guide wire. A guide wire 14 can also be inserted in one of the above-mentioned channels so the other devices like a wire basket 82 or a balloon 80 can be advanced over it until the balloon catheter emerges at the distal end of the device while still tracking over the wire, providing support to the balloon or basket catheter. Inflation of the balloon (or deployment of the basket) can be done while the wire is present or without the wire. The presently preferred method is with the wire to provide support to maintain balloon (or basket) position.

With further reference to FIG. 9, it will be noted that this apparatus for temporarily reducing motion of at least one leaflet 16 in a heart valve in a patient's beating heart comprises an elongated structure 30 insertable into the patient to a location adjacent the heart valve. Elongated structure 30 contains a leaflet stabilization structure 82 that is deployable from the elongated structure into contact with the at least one leaflet 16. The leaflet stabilization structure comprises a mesh 82 of wires. Mesh 82 is resiliently biased to expand into contact with the at least one leaflet 16 (when the mesh is deployed from elongated structure 30) to apply mechanical pressure to the leaflet, while allowing blood to flow through the mesh. Typically, the heart valve includes at least two leaflets 16 (e.g., on the left and on the right, respectively, in FIG. 9). Mesh 82 is then typically deployable from elongated structure 30 between those leaflets. Typically, when mesh 82 is thus deployed between the leaflets, mesh 82 resiliently expands to push the leaflets apart, but allows blood to flow through the valve through the mesh. When no longer needed, mesh 82 may be collapsible back into elongated structure 30 for removal from the patient.

Figure 10:
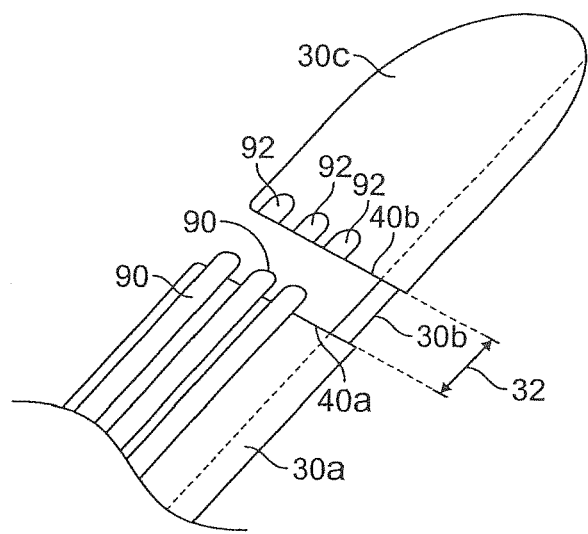
FIG. 10 is a simplified elevational view similar to a portion of FIG. 1 for another illustrative embodiment of the invention.

FIG. 10 shows an illustrative embodiment of how apparatus 10 may be constructed to detect the presence of leaflet tissue at various locations between jaw surfaces 40a and 40b. In this embodiment jaw surface 40a has a plurality of pins 90 extending distally from it. Each of pins 90 is disposed in the proximal portion 30a of elongated shaft 30, and each of pins 90 has a longitudinal axis that is substantially parallel to the longitudinal axis of the shaft. Each pin 90 is resiliently biased to project a short distance (in the distal direction) from proximal jaw surface 40a. Opposite the distal end of each pin 90, distal jaw surface 40b has a respective recess 92 that is large enough and deep enough to receive the end of the associated pin 90 without proximally displacing that pin when jaws 40a and 40b are closed with no leaflet tissue between the jaws. However, when jaws 40 are closed on tissue, that tissue will proximally displace any one or more of pins 90, the distal ends of which contact that tissue. Any others of pins 90 that do not contact tissue will not be proximally displaced. An electrical circuit associated with each of pins 90 can detect whether or not the associated pin has been proximally displaced and can change the illumination of a respective one of the lights 62 in display 60. The pattern of lights 62 can be similar to the arrangement of pins. In this way the pattern of illumination of display 60 can indicate where and/or to what extent leaflet tissue has been captured between jaws 40.

Figure 11:
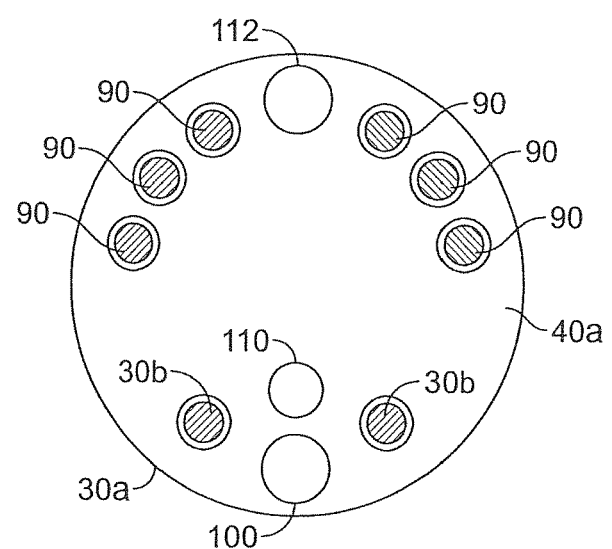
FIG. 11 is a simplified cross-sectional view of a structure like that shown in FIG. 10 in accordance with the invention.

FIG. 11 shows an end view of jaw surface 40a in an illustrative embodiment. FIG. 11 shows pins 90 in an arc around the side of jaw surface 40a that is diametrically across that surface from two movable links 30b between shaft portions 30a and 30c. These are the links that support distal shaft portion 30c relative to proximal shaft portion 30a, and that are axially movable to allow distal shaft portion 30c to move distally away from or proximally toward axial shaft portion 30a to open or close jaws 40. (Double-headed arrow 32 in FIG. 10 indicates the nature of this motion.) The axial motion of links 30b is controlled by squeezing together or releasing handle portions 20a and 20b (assuming a handle construction like that shown in FIG. 1). Other features visible in FIG. 11 are (1) guide wire lumen 100 (for guide wire 14), (2) suture lumen 110 (for one leg of the suture material that is used as a tether for the patient's heart valve leaflet), and (3) needle lumen 112 (for the needle that is used to pass the suture through the leaflet to tether it).

Figure 12:
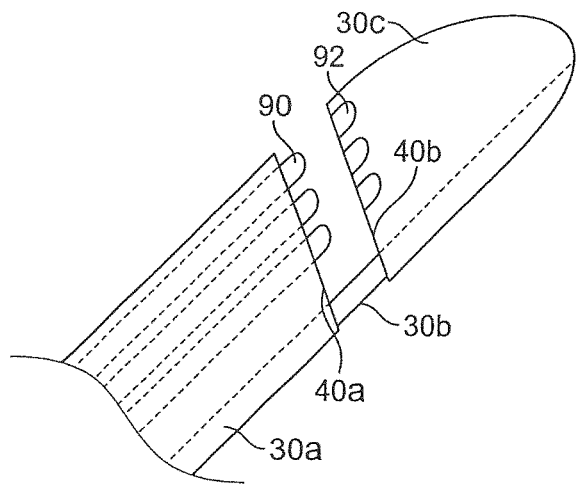
FIG. 12 is again similar to FIG. 10 for another illustrative embodiment of the invention.

Note that FIG. 10 shows jaw surfaces 40 having a different angle of inclination than is shown in FIG. 1. FIG. 12 shows some of the structures from FIG. 10 in an embodiment with jaw surfaces 40 inclined as shown in FIG. 1. In FIGS. 1 and 12, jaw surfaces 40 are inclined in the distal direction as one proceeds along those surfaces moving away from links 30b. In FIG. 10, jaw surfaces 40 are inclined in the proximal direction as one proceeds along those surfaces moving away from links 30b.

Figure 13:
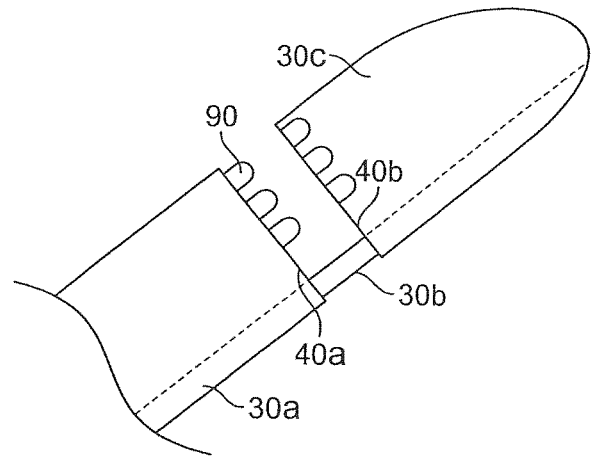
FIGS. 13-17 are each similar to FIG. 12 for various other illustrative embodiments of the invention.
Figure 14:
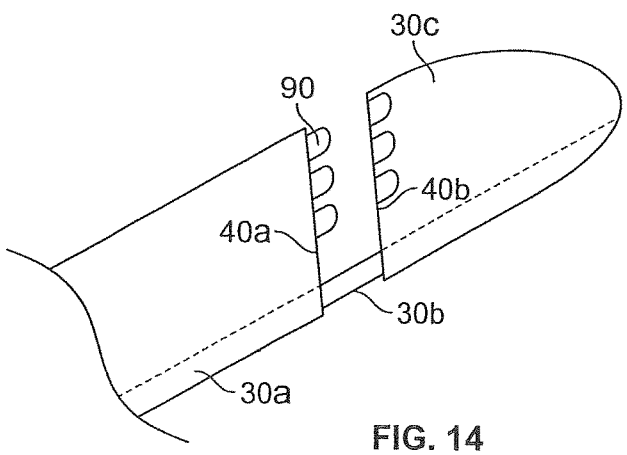
Figure 15:
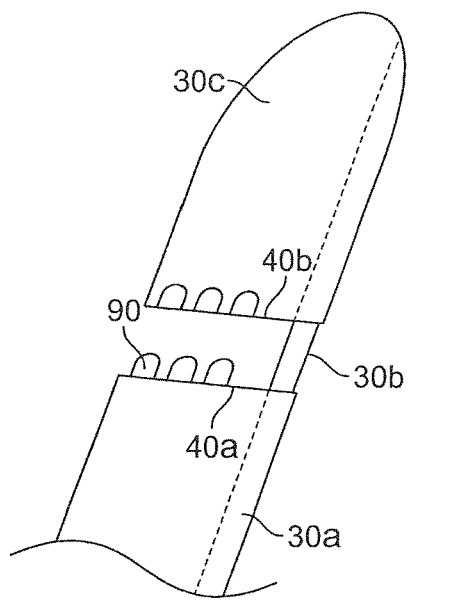

FIG. 13 shows another possibility in which jaw surfaces 40a and 40b are each substantially perpendicular to the longitudinal axis of elongated shaft 30. FIG. 14 shows again a configuration like that shown in FIGS. 1 and 12. FIG. 15 shows again a configuration like that shown in FIG. 10.

Figure 16:
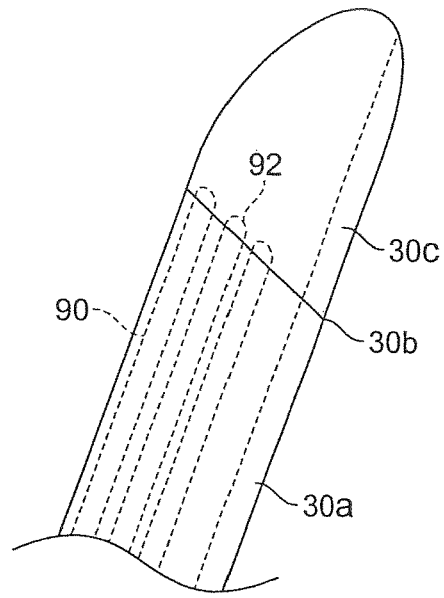
Figure 17:
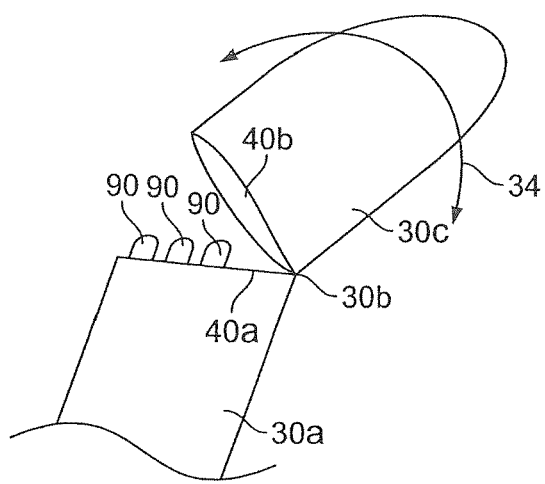

FIGS. 16 and 17 show an alternative embodiment in which the distal portion 30c of the elongated shaft is pivotable about a pivot 30b to open or close the jaws. In other respects the embodiment of FIGS. 16 and 17 can be like other embodiments shown and described herein.

Figure 18:
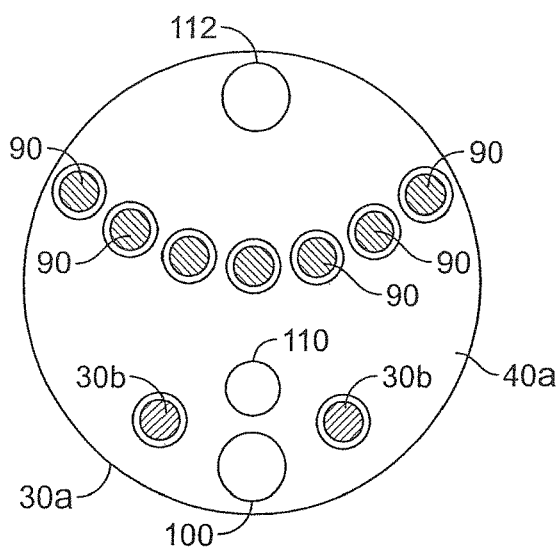
FIGS. 18-20 are each similar to FIG. 11 for various other illustrative embodiments of the invention.
Figure 19:
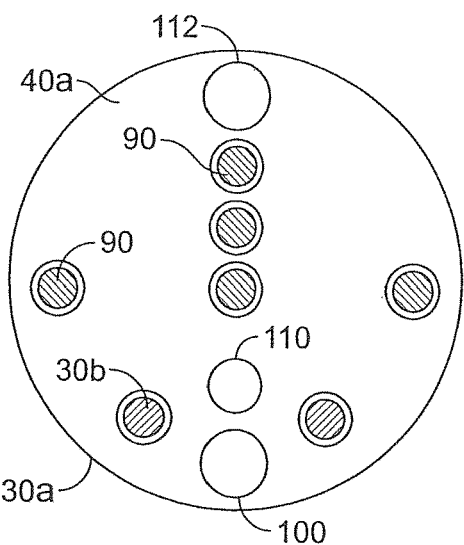
Figure 20:
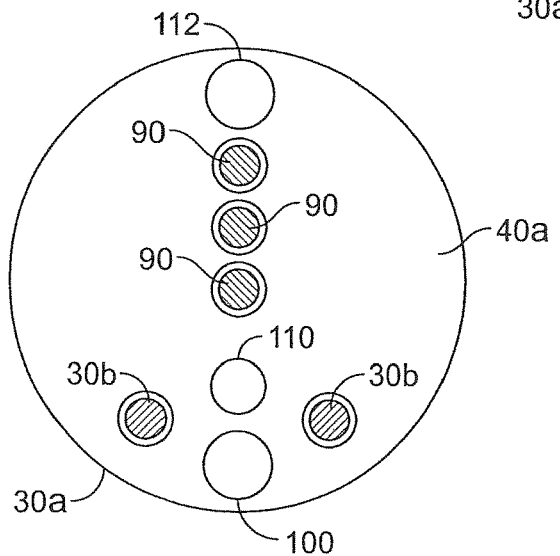

FIGS. 18-20 show other illustrative arrangements of pins 90 for detecting tissue between jaws 40a and 40b. In FIG. 18, pins 90 are arranged in an arc around needle lumen 112. (In contrast, in FIG. 11 the center of the arc of pins 90 is approximately the center of jaw surface 40a. In FIG. 18 the center of the arc of pins 90 is closer to the outer peripheral edge of jaw surface 40a.) In FIG. 20, pins 90 are arranged in a straight line that is radial of jaw surface 40a (e.g., from about the center of the jaw surface to needle lumen 112). FIG. 19 is similar to FIG. 20, but with the addition of two more pins near respective opposite ends of a diameter of jaw surface 40a that is substantially perpendicular to the above-mentioned radius. In respects other than the arrangement of pins 90, FIGS. 18-20 can be similar to FIG. 11. It will be apparent how the various arrangements of pins 90 in FIGS. 11 and 18-20 can be used to detect the presence (or absence) of leaflet tissue at various locations between jaw surfaces 40a and 40b. The display 60 used with each arrangement of pins 90 can have lights 62 in arrangements similar to the pin arrangement so that these lights convey to the user of the apparatus which pins 90 are engaging leaflet tissue and which pins 90 are not engaging leaflet tissue.

Figure 21:
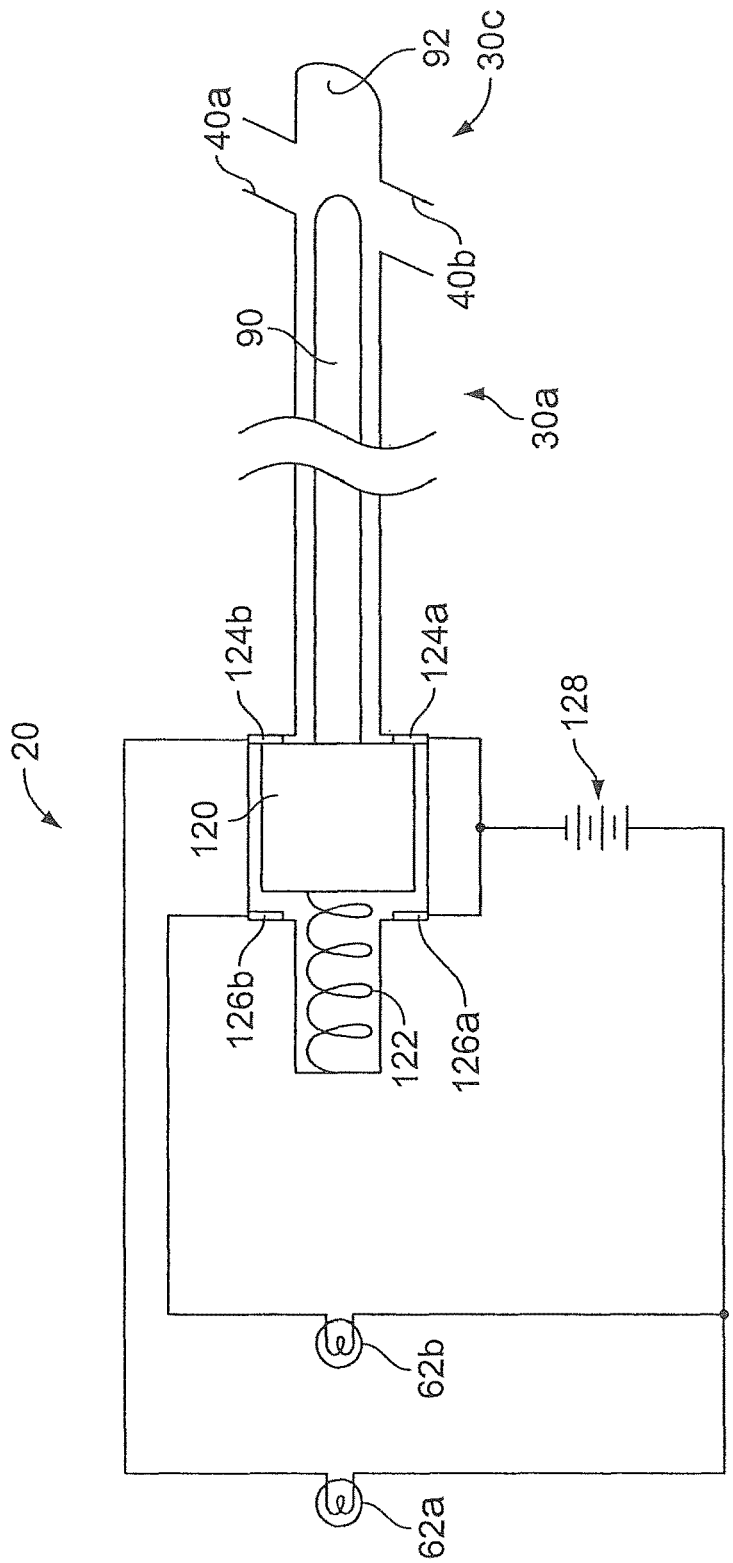
FIG. 21 is a simplified electromechanical schematic block diagram of an illustrative embodiment of apparatus in accordance with the invention.

FIG. 21 shows an illustrative embodiment of circuitry and other structure associated with a representative one of tissue-detecting pins 90. As shown in FIG. 21, pin 90 is resiliently urged to move in the distal direction by prestressed compression coil spring 122 pushing in the distal direction on the proximal head 120 of the pin. When there is no tissue clamped between jaw surfaces 40a and 40b at the distal end of pin 90, the head 120 of the pin can move all the way to the right, where it completes an electrical connection between electrical contacts 124a and 124b as shown in FIG. 21. This completes an electrical circuit from battery 128, through elements 124a, 120, 124b, and 62a, and back to battery 128. Light 62a is thereby illuminated. There is no comparable complete circuit for light 62b, and so light 62b is not illuminated. On the other hand, if there is tissue clamped between jaw surfaces 40a and 40b at the distal end of pin 90, then that tissue pushes pin 90 in the proximal direction. This causes pin head 120 to move away from electrical contacts 124a and 124b, and to instead make an electrical connection between contacts 126a and 126b. Light 62a is thereby extinguished (turned off) and light 62b is instead turned on. Lights 62a and 62b may be of different colors (e.g., red and green, respectively). Both of these lights may be visible at the same one of the light locations 62 in display 60. Therefore, the color visible in that light location will be red if no tissue is present at the distal end of pin 90, and it will be green if there is tissue present at the distal end of that pin. The operator of the apparatus can therefore tell where tissue is present by which of light locations 62 in the display 60 is showing which color. (The particular colors mentioned here are only examples, and other colors can be used instead if preferred.)

Figure 22A:
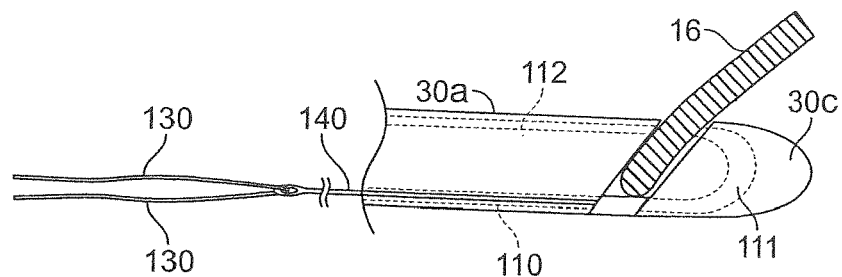
FIGS. 22A-F are a simplified collection of partial elevational views showing successive stages in an illustrative embodiment of use of apparatus in accordance with the invention.
Figure 22B:
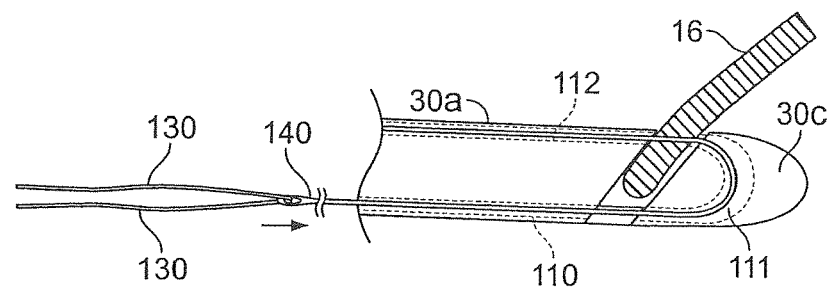
Figure 22C:
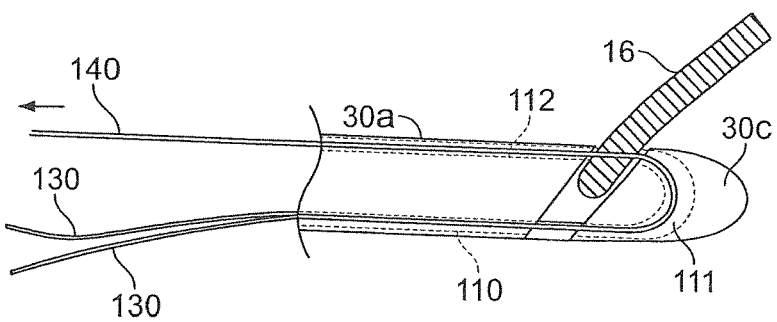
Figure 22D:
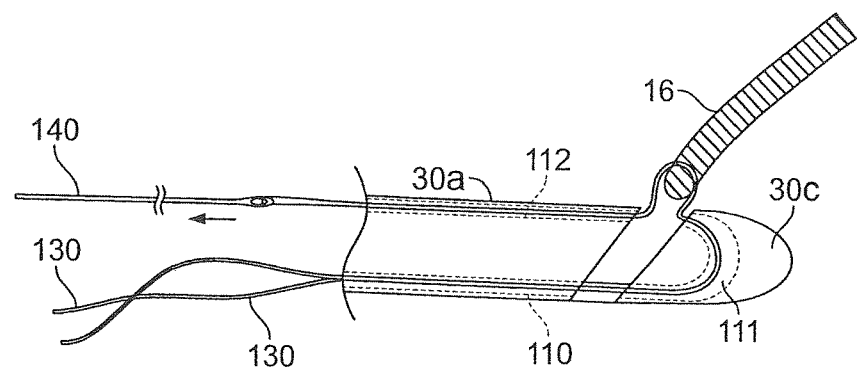
Figure 22E:
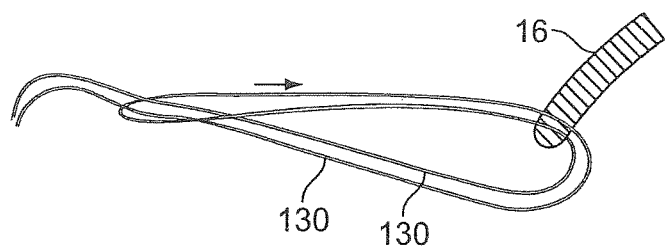
Figure 22F:
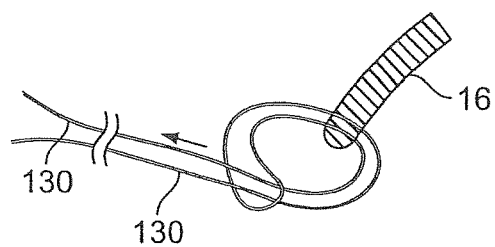

FIGS. 22A-F show an illustrative embodiment of use of apparatus 10 to attach a length of suture 130 (as a tether) to a patient's heart valve leaflet 16. In FIG. 22A an otherwise free edge portion of leaflet 16 is clamped between the jaws 40 of apparatus 10. A very long and laterally flexible needle 140 is inserted into suture lumen 110 from a proximal portion of apparatus 10. A folded over, doubled strand of suture material 130 is threaded through the proximal eye of needle 140. Pushing from the proximal portion of needle 140 that is proximal of handle 20, the distal portion of the needle passes along suture lumen 110 in proximal shaft portion 30a, and from that lumen into U-shaped, direction-reversing lumen 111 in distal shaft portion 30c. Direction-reversing lumen 111 guides the distal portion of needle 140 to reverse direction (from distally moving to proximally moving), and also repositions it laterally so that it can pass through leaflet tissue 16 and enter needle lumen 112 (in shaft portion 30a again) going in the proximal direction (see FIG. 22B). Eventually, what was the distal end of needle 140 emerges from apparatus 10 proximally of handle 20 and can be pulled proximally to continue the motion of needle 140 through apparatus 10. This pulling of needle 140 pulls suture 130 into apparatus 10 (FIG. 22C) and ultimately also back out of the apparatus. Leaflet 16 can now be released from jaws 40 (FIG. 22D), and needle 140 can be removed from suture 130. Apparatus 10 can be removed from the patient, and suture 130 can be freed from the apparatus. The free ends of suture 130 are passed through the doubled-back portion of the suture (FIG. 22E). The free ends of suture 130 are then pulled proximally to cause the doubled-back portion of the suture to travel into the patient so that a small suture loop is formed through and around the otherwise free edge portion of leaflet 16 (FIG. 22F). A proximal portion of suture 130 can be secured to another portion of the patient's heart (e.g., where apparatus 10 entered the apex of the heart (see FIG. 43)) so that the suture extending between leaflet 16 and that other attachment point acts as an artificial prosthetic chorda or tether of appropriate length to help the proper functioning of leaflet 16. (The entry point of apparatus 10 into the heart is, of course, closed as the procedure concludes, as is the entry point of the apparatus into the patient.) The procedure is preferably performed on a beating heart so that the best length for the tether can be determined by observing (e.g., fluoroscopically) the effect of several possible tether lengths. When the best length is decided upon, anchoring of suture 130 to the heart at that length from leaflet 16 is completed, excess suture 130 outside the patient's heart is cut away and removed from the patient, and the patient is closed as described above.

Figure 23:
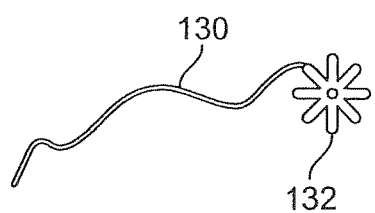
FIG. 23 is a simplified elevational view of an illustrative embodiment of other possible apparatus in accordance with the invention.
Figure 24:
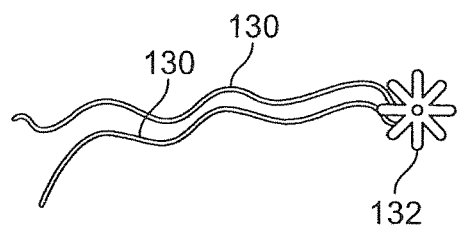
FIG. 24 is similar to FIG. 23 for another illustrative embodiment in accordance with the invention.

FIG. 23 illustrates an alternative leaflet tether structure in accordance with the invention. This is a length of suture material (e.g., of GORE-TEX®) attached at its distal end to a collapsible/expandable metal (e.g., nitinol) clip or anchor 132. Another alternative is shown in FIG. 24, which includes a double suture 130 attached to anchor 132. In subsequent FIGS. the simpler FIG. 23 embodiment will generally be shown, but it will be understood that the FIG. 24 embodiment can be used instead if desired.

Figure 29:
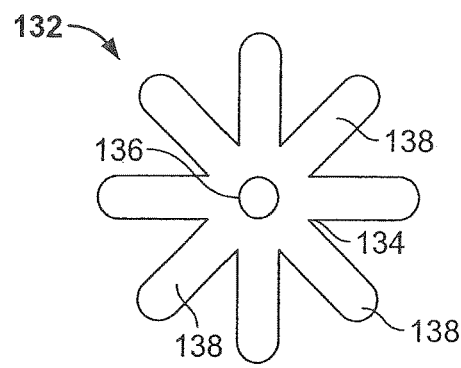
FIG. 29 is a simplified elevational view, from another angle, of apparatus of the type shown in FIG. 23 or 24.

As can perhaps best be seen in FIG. 29, anchor 132 has a central body 134, through which there is an aperture 136 for facilitating attachment of suture 130. A plurality of arms 138 radiate outward from central body 134 when anchor 132 is unconstrained by other apparatus. Arms 138 can be elastically collapsed toward one another to make anchor 132 temporarily much smaller for passage through the tissue of a heart valve leaflet 16. After such passage through leaflet tissue, arms 138 can be released from constraint. This allows them to resiliently return to the shape shown in FIG. 29. In this configuration, anchor 132 resists being pulled back through the leaflet tissue, and so anchor 132 anchors the distal end of suture 130 to the leaflet.

Figure 25A:
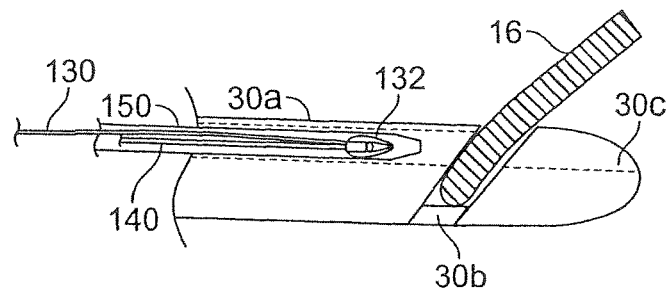
FIGS. 25A-C are a simplified collection of partial elevational views showing successive stages in an illustrative embodiment of use of apparatus of the type shown in FIG. 23 or 24 in accordance with the invention.
Figure 25B:
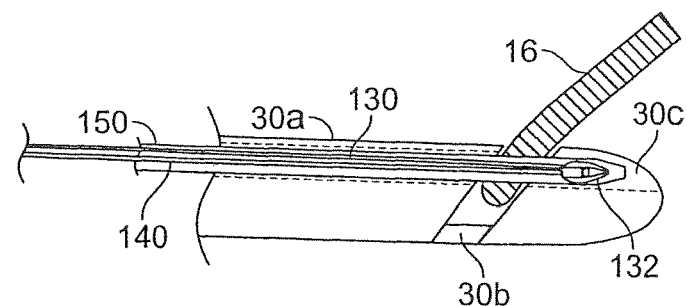
Figure 25C:
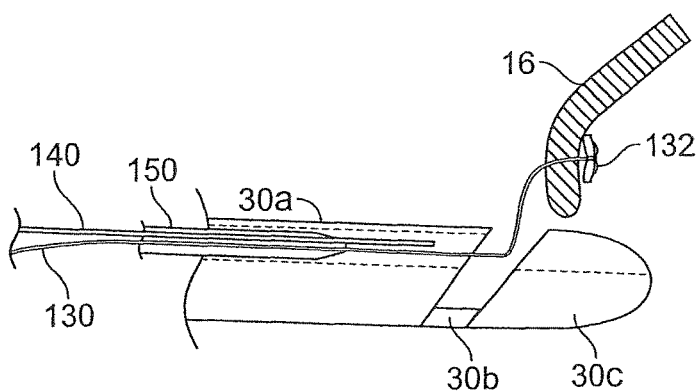

FIGS. 25A-C show a sequence in which apparatus 10 is used to tether a heart valve leaflet 16 using a tether structure like that shown in FIG. 23 or FIG. 24. In FIG. 25A leaflet 16 is captured between the jaws 40 near the distal end of shaft 30. Tether structure 130/132 is pushed distally along a needle lumen 112 using needle 140 until anchor 132 has passed through leaflet tissue 16 (FIG. 25B). After passing through tissue 16, anchor 132 can enter a space in distal shaft portion 30c that is large enough to allow the anchor to return to its FIG. 29 shape. Needle 140 can then be retracted proximally. Anchor 132 remains on the distal side of leaflet 16 because the larger (FIG. 29) shape of the anchor resists movement of the anchor back through leaflet 16. Leaflet 16 can then be released from apparatus 10 as shown in FIG. 25C, and the apparatus can be withdrawn from the patient, leaving the distal end of tether structure 130/132 attached to leaflet 16.

Figure 27:
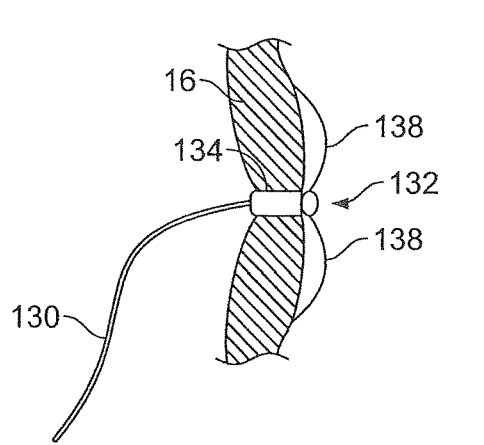
FIG. 27 is a simplified view, partly in section, showing illustrative use of apparatus of the type shown in FIG. 23 or 24 in accordance with the invention.
Figure 28:
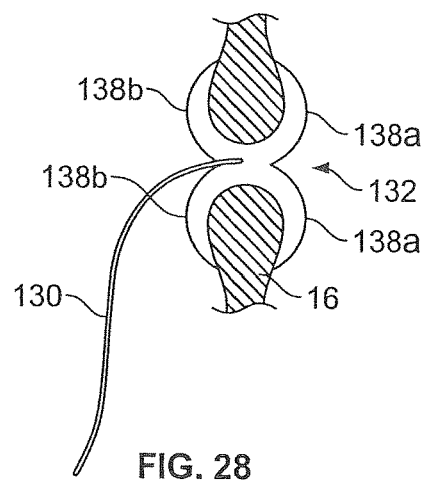
FIG. 28 is similar to FIG. 27 for another illustrative embodiment in accordance with the invention.

A detail of how tether structure 130/132 may be attached to leaflet 16 is shown in FIG. 27. An alternative embodiment of this detail is shown in FIG. 28. In the FIG. 28 alternative, anchor 132 has two sets of arms 138a and 138b. These two sets of arms are spaced from one another along a central body 134 of the anchor so that when the anchor is deployed, set 138a can be distal of leaflet tissue 16, and set 138b can be proximal of that leaflet tissue (resiliently trapping the leaflet tissue between the two sets of arms). This may provide even more secure anchoring of the distal end of suture 130 to leaflet 16 by anchor 132.

Figure 26A:
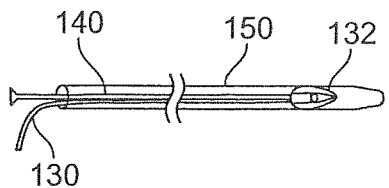
FIGS. 26A-C are a simplified collection of partial elevational views showing illustrative further apparatus and use thereof in accordance with the invention.
Figure 26B:
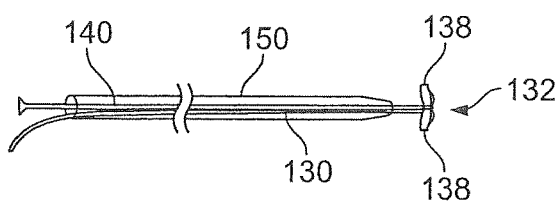
Figure 26C:
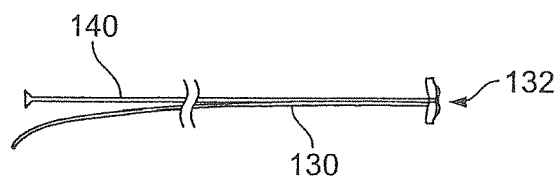

FIGS. 26A-C show an illustrative embodiment of apparatus in accordance with the invention that can be used to facilitate deployment of a tether structure like that shown in any of FIGS. 23-25 and 27-29. In the alternative shown in FIGS. 26A-C, anchor 132, suture 130, and needle 140 are all disposed in an elongated sheath 150 (FIG. 26A). Sheath 150 is slender enough to keep the arms 138 of anchor 132 collapsed to their relatively small size. Sheath 150 is also slender enough to pass axially along the needle lumen 112 of apparatus 10 to reach the location of a leaflet 16 clamped in apparatus 10. Sheath 150 may have a sufficiently sharp distal end and sufficient axial "pushability" to be pushed through the clamped leaflet tissue. Needle 140 can then be used to push anchor 132 in the distal direction out of an aperture in the distal end of sheath 150 (FIG. 26B). This allows arms 138 to resiliently spread out. Sheath 150 and needle 140 then can be withdrawn (FIG. 26C).

The use of sheath 150 can help keep anchor 132 confined to its relatively small size as it passes distally along needle lumen 112 (and even as it passes in the distal direction through leaflet tissue 16 if sheath 150 is configured to pass through leaflet tissue 16).

Figure 30:
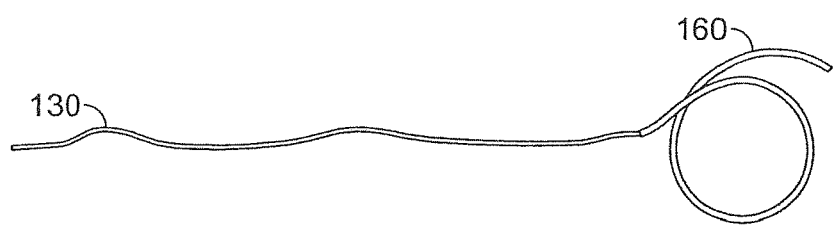
FIG. 30 is a simplified elevational view of another illustrative embodiment of possible apparatus in accordance with the invention.

FIG. 30 shows another illustrative embodiment of a tether structure in accordance with the invention. In FIG. 30, the distal end of suture 130 is attached to an anchor 160 in the form of a coil of wire (e.g., of nitinol). Anchor 160 is resiliently biased to form a coil like that shown in FIG. 30 (or FIG. 32), but it can be elastically deformed to be temporarily relatively straight (e.g., as shown in FIG. 31A).

Figure 31A:
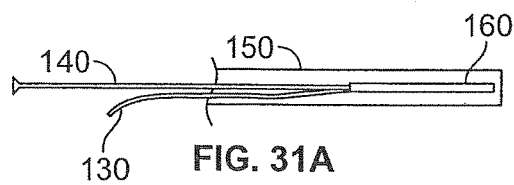
FIGS. 31A-C are a simplified collection of partial elevational views showing illustrative further apparatus and use thereof in accordance with the invention.
Figure 31C:
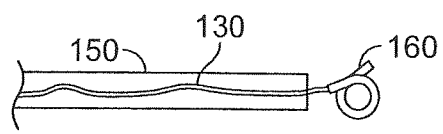
Figure 31B:
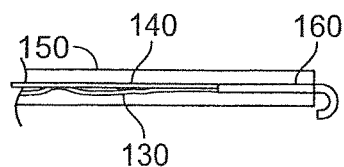
Figure 32:
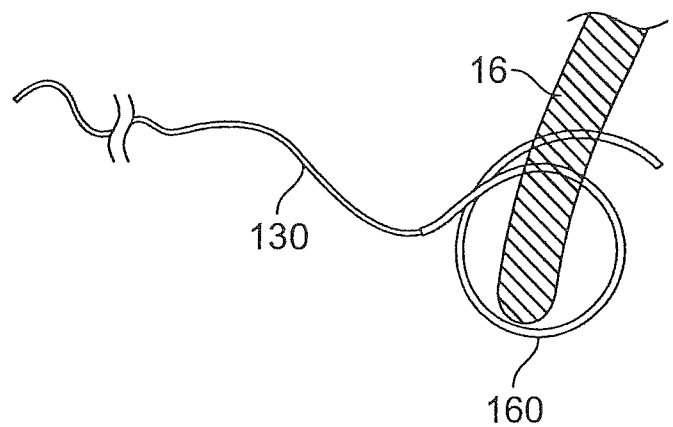
FIG. 32 is a simplified view, partly in section, showing illustrative use of apparatus of the type shown in FIG. 30 in accordance with the invention.

FIG. 31A shows anchor 160 straightened out in the distal portion of a hollow tubular sheath 150. Suture 130 extends proximally back from anchor 160, and needle 140 is insertable axially into sheath 150 to push anchor 160 distally out of the distal end of sheath 150 when it is desired to deploy the anchor. This is typically done when the distal end of sheath 150 is against leaflet tissue that has been clamped in apparatus 10. Sheath 150 and its contents may be inserted axially into needle lumen 112 in apparatus 10 to get the distal end of sheath 150 to the clamped leaflet tissue. FIG. 31B shows anchor 160 being pushed out of the distal end of sheath 150, which causes anchor 160 to begin to pass through leaflet tissue (not shown) at the distal end of the sheath, and which also allows anchor 160 to begin to resiliently return to its coiled condition. When anchor 160 has been fully pushed out of sheath 150 (FIG. 31C), it returns fully to its coil shape, in which it is looped through or around leaflet tissue 16 (see FIG. 32). In this condition, anchor 160 firmly secures suture 130 to leaflet 16 and resists pulling out of the leaflet.

Figure 33:
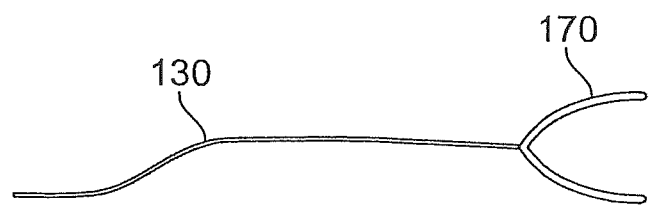
FIG. 33 is a simplified elevational view of still another illustrative embodiment of possible apparatus in accordance with the invention.
Figure 34:
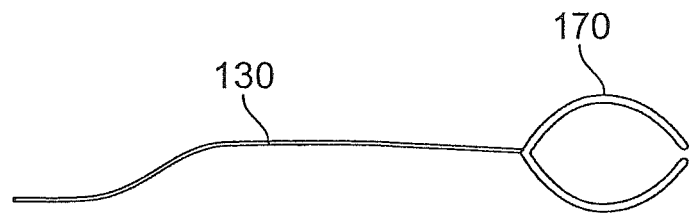
FIG. 34 is similar to FIG. 33 for another operating condition of the FIG. 33 apparatus.

FIGS. 33 and 34 show yet another illustrative embodiment of a tether structure in accordance with the invention. FIG. 33 shows the undeployed condition of this tether structure, and FIG. 34 shows its deployed condition. This tether structure includes a resilient spring clip 170 attached to a distal end of suture 130. Clip 170 is resiliently biased to close to the C shape shown in FIG. 34, but it can be elastically deformed to the more open U shape shown in FIG. 33.

Figure 35A:
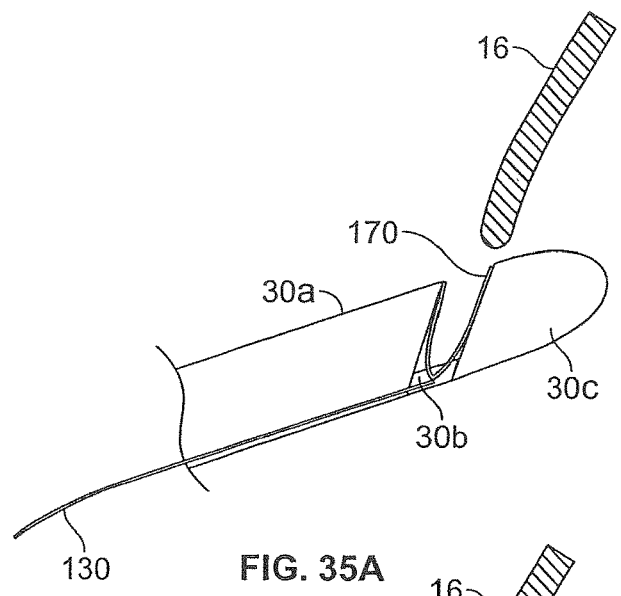
FIGS. 35A-C are a simplified collection of partial elevational views showing illustrative further apparatus and use thereof in accordance with the invention.
Figure 35B:
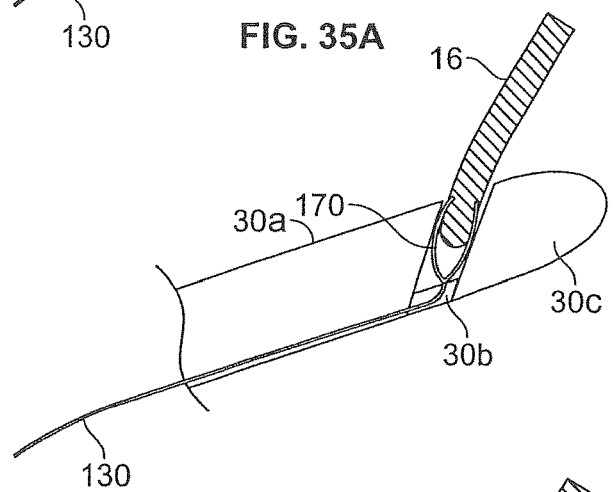
Figure 35C:
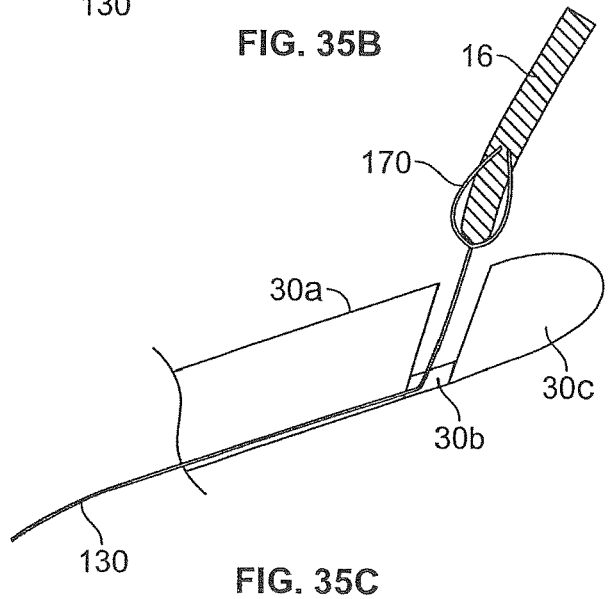

FIGS. 35A-C show that clip 170 is initially disposed in apparatus 10 with each leg of the clip adjacent a respective one of the jaw surfaces 40 in that apparatus (FIG. 35A). Suture 130 initially extends proximally from clip 170 through suture lumen 110 in elongated shaft 30. Each leg of clip 170 is initially releasably secured to the associated jaw 40 (see FIGS. 36-38 for some examples of how this may be done). After leaflet tissue 16 has been captured between jaws 40 (and therefore between the arms of clip 170), the clip arms may be released from jaws 40. This allows the arms of clip 170 to resiliently close on tissue 16, thereby securing tether structure 130/170 to the leaflet tissue (FIG. 35B). Leaflet 16, with tether structure 130/170 attached, can now be released from jaws 40 (FIG. 35C), and apparatus 10 can be withdrawn.

Figure 36:
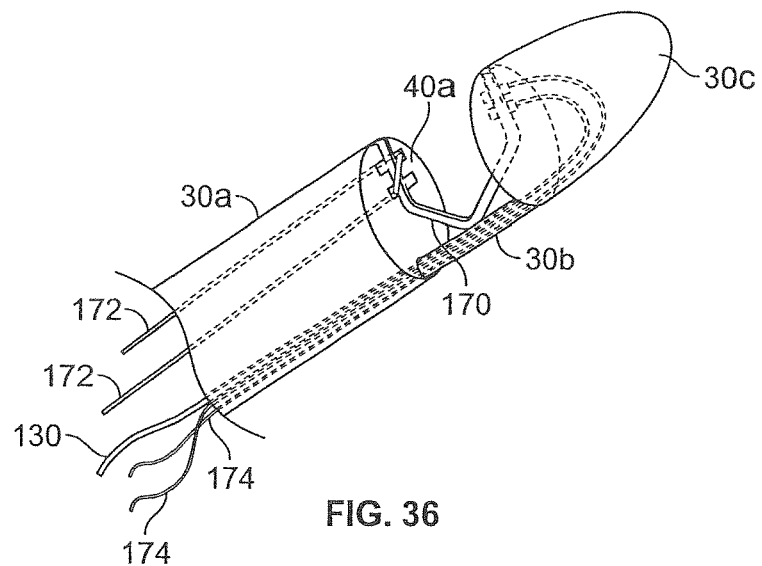
FIG. 36 is a simplified, partial, isometric or perspective view of apparatus of the general type shown in FIG. 35, but including an illustrative embodiment of possible additional features in accordance with the invention.

FIG. 36 shows an illustrative embodiment of apparatus for releasably holding each arm of clip 170 to the associated jaw surface 40 prior to release and deployment of the clip. In this embodiment, this is done by a first holder suture 172 for the proximal arm 10 of clip 170, and by a second holder suture 174 for the distal arm of the clip. (In these instances, the word suture is used as a generic term for any suitable cord or strand of material. Indeed, throughout this specification the word suture tends to be used in this general or generic sense.) Holder suture 172 is looped around the proximal arm of clip 170 and is held tight to hold that arm against proximal jaw surface 40a. Holder suture 174 is routed through linking structure 30b to distal shaft portion 30c, within which suture 174 is directed back to loop around the distal arm of clip 170. Suture 174 is held tight to hold the distal arm of clip 170 against distal jaw surface 40b. When it is desired to deploy clip 170, each of holder sutures 172 and 174 can be cut. This releases both clip arms from jaw surfaces 40 and allows the clip to resiliently close on tissue between the jaws.

Figure 37:
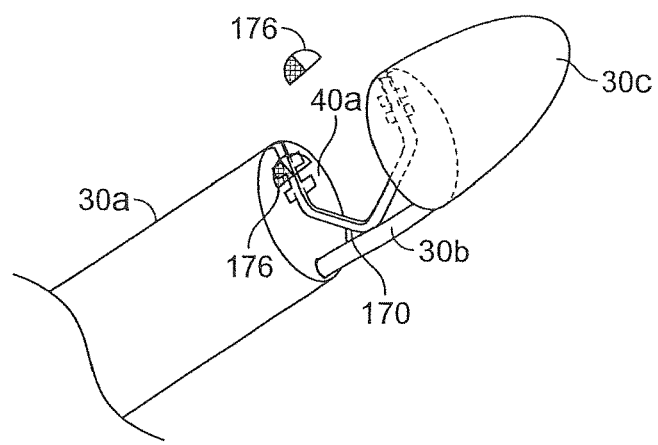
FIGS. 37 and 38 are generally similar to FIG. 36 for another illustrative embodiment of possible additional features in accordance with the invention.
Figure 38:
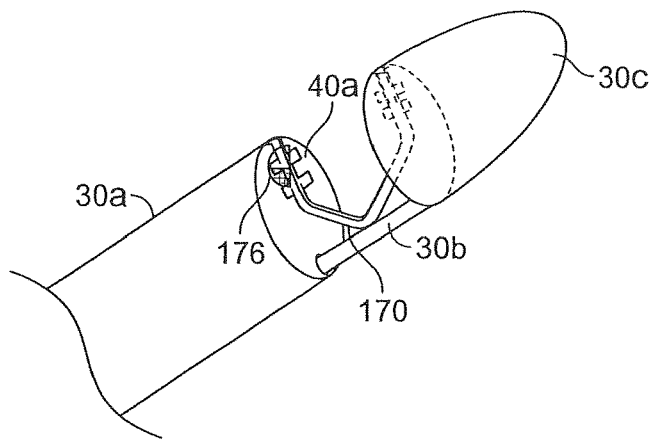

FIGS. 37 and 38 show an alternative embodiment in which rotating retainers 176 are used to releasably hold each arm of clip 170 to the associated jaw surface 40. In FIG. 37, representative retainer 176 is rotated clockwise to extend over the proximal arm of clip 170 and to thereby hold that clip arm to proximal jaw surface 40. In FIG. 38, representative retainer 176 is rotated counter-clockwise to no longer extend over the proximal clip arm and to thereby release that clip arm. A similar structural arrangement may be used for the distal arm of clip 170. Retainer 176 may be rotated as described above by being connected to rotatable shafts that extend axially through elongated shaft 30.

Figure 39:
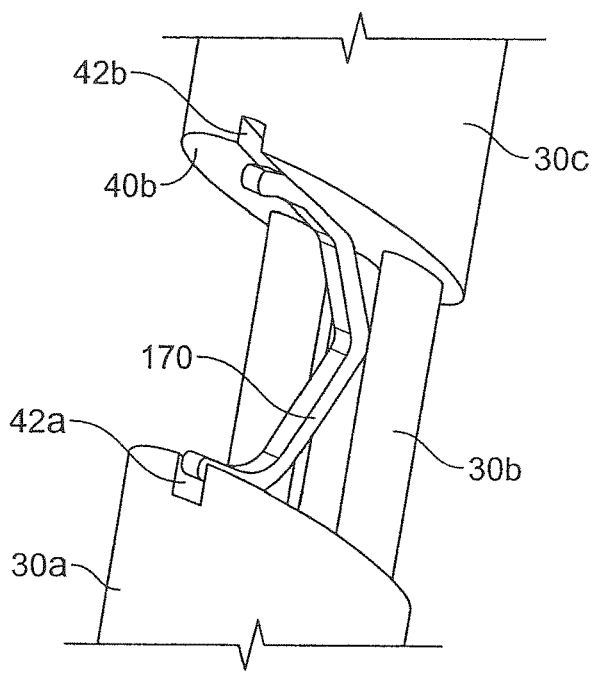
FIG. 39 is a simplified, partial, perspective or isometric view of another illustrative embodiment of possible features in accordance with the invention.

FIG. 39 shows that a clip like 170 may be further stabilized relative to jaw surfaces 40a and 40b by having each arm of the clip releasably received in a recess 42a/42b in the surface of the jaw which that clip arm is adjacent to prior to deployment.

Figure 40:
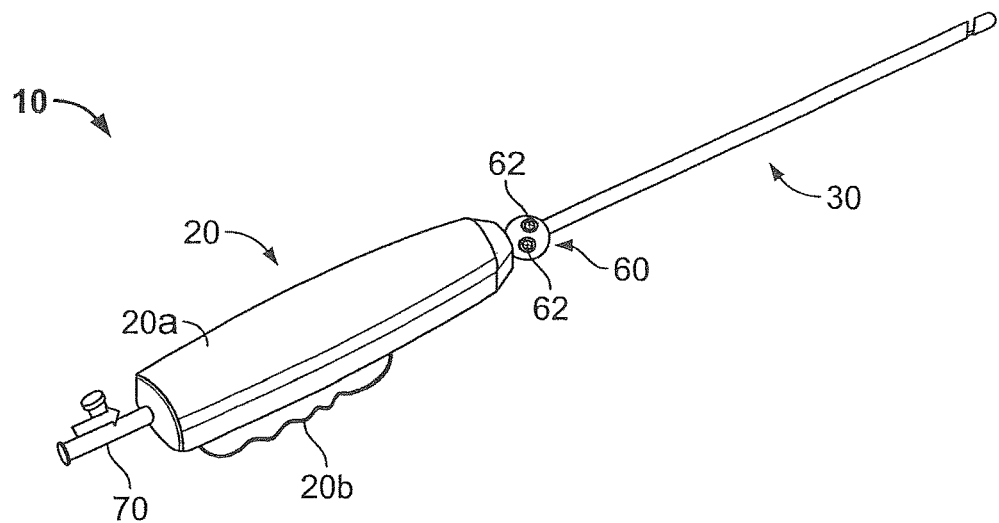
FIG. 40 is a simplified isometric or perspective view of another illustrative embodiment of apparatus in accordance with the invention.

FIG. 40 further illustrates, among other features, the concept of a display 60 that is rotatable about the longitudinal axis of apparatus 10.

Figure 41:
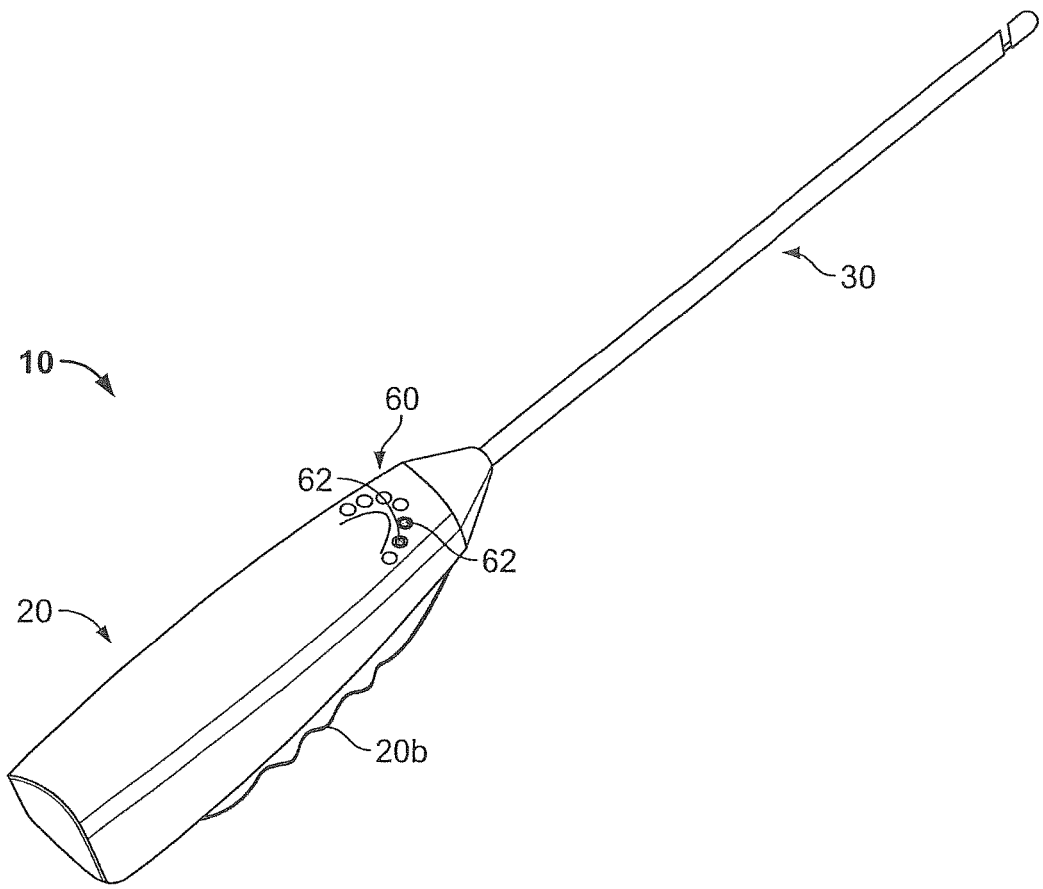
FIG. 41 is a simplified isometric or perspective view of still another illustrative embodiment of apparatus in accordance with the invention.

FIG. 41 shows another illustrative embodiment including, among other features, a non-rotational display 60 and a depressable lever 20b as the bottom housing half of the handle 20.

Figure 42:
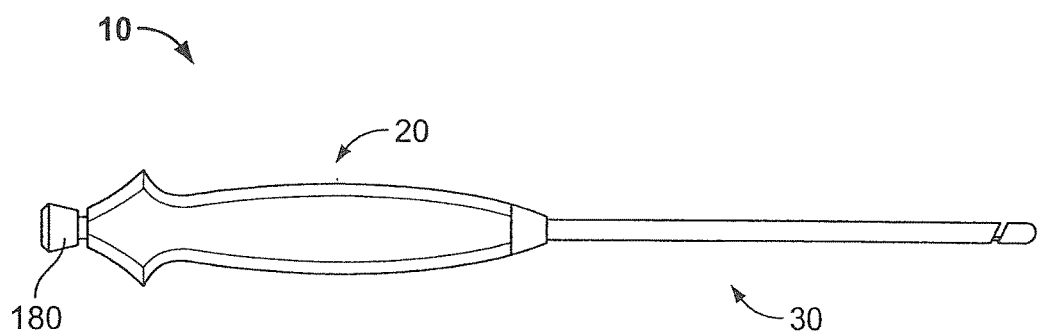
FIG. 42 is a simplified elevational view of yet another illustrative embodiment of apparatus in accordance with the invention.

FIG. 42 shows yet another illustrative embodiment including, among other features, a proximal button 180 that can be pressed inwardly (i.e., in the distal direction) when it is desired to open the distal jaws 40 to admit the tissue of a leaflet between those jaws. The jaws are normally closed and are resiliently biased to that closed position. But when proximal button 180 is pushed in, the distal jaws open. When proximal button 180 is again released, the jaws attempt to resiliently re-close. If no leaflet tissue is between the jaws when this happens, the jaws will fully re-close. If leaflet tissue is between the jaws when the proximal button is released, that tissue will be resiliently clamped by the jaws.

Figure 43:
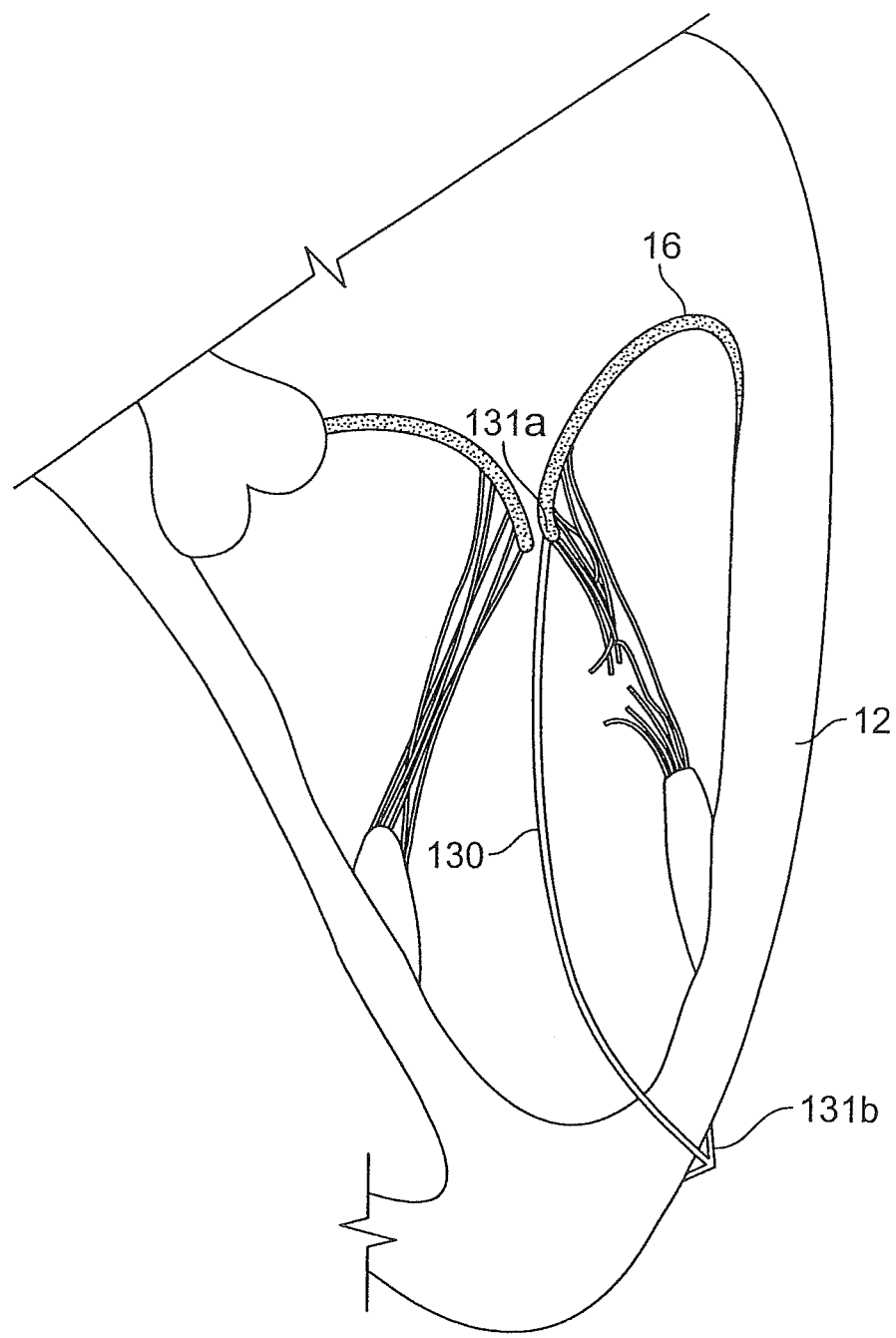
FIG. 43 is a simplified schematic view of an illustrative embodiment of use of the invention.

For completeness, FIG. 43 shows that tether 130, which is attached to heart valve leaflet 16 at 131a (e.g., in any of the ways described elsewhere in this specification), is attached at its other end (i.e., at 131b) to another portion of the patient's heart 12. For example, this other portion of the patient's heart may be at or near the point at which the elongated shaft 30 of instrument 10 was introduced into the heart (e.g., as described above in connection with FIG. 1).

Recapitulating and extending the above, the present invention typically involves use of an articulating, hand-held instrument that contains a pre-loaded suture (e.g., GORE-TEX® suture). This suture can be delivered and attached to a mitral or tricuspid valve leaflet while the heart is beating.

The instrument's shaft is typically introduced through a small incision in the 4th or 5th intercostal space, and then through the apex of the heart. Then the instrument is advanced under echocardiogram and/or fluoroscopic guidance into close proximity to the affected mitral or tricuspid valve leaflet. Using this visualization guidance, the leaflet is grasped with jaws of the instrument tip. Unlike the '694 reference approach, additional devices and accessories (such as inflatable balloons or expandable wire baskets) can be introduced and advanced through a special port (channel) in the instrument shaft to reach and help stabilize the coapting leaflet. This can be done in preparation for leaflet capture and suture deployment.

Once the leaflet is captured in the appropriate orientation, a needle can be advanced through the instrument shaft. The needle can puncture the leaflet and hook a looped suture (e.g., as in the '694 reference). The needle and instrument can then be retracted from the heart, pulling with them the looped end of the suture outside of the heart and the patient's body. The two free ends of the suture can then be inserted into the looped end and pulled such that the loop travels toward the leaflet and is cinched there. This creates a desirable low-profile knot at the leaflet puncture site. Other possible means of deploying and attaching the suture to the leaflet have been described earlier in this specification and are briefly recapitulated in the next several paragraphs.

As shown in FIG. 22 of the accompanying drawings, a long needle (e.g., of nitinol) with a pre-attached suture (e.g., of GORE-TEX®) can be advanced through either of two parallel channels (ports) in the instrument shaft. Once the needle reaches the distal jaw of the instrument, it will follow the contour of the path and will track around a specially designed path in the distal jaw such that it can puncture the leaflet tissue between the jaw surfaces. The needle is then further advanced until it emerges from the proximal end of the device. The needle can then be pulled proximally until access to the attached suture can be attained. The needle can now be removed from the suture, and the suture free ends can be inserted as described earlier into the looped portion to create the desired knot.

Another illustrative suture deployment embodiment can be achieved by utilizing a star-shaped, self-expanding clip (e.g., of nitinol) with pre-attached suture material (e.g., of GORE-TEX®) as shown in FIGS. 23-29 of the accompanying drawings. The clip is initially folded in a constrained and streamlined fashion in preparation for advancement, puncture of the leaflet, and deployment on the other side of the leaflet. Deployment and release of the star clip can be accomplished by proximally withdrawing a constraining sheath, which also passed through the leaflet puncture site. The instrument can then be withdrawn, leaving behind the deployed clip and attached suture.

Still another illustrative suture deployment approach uses a C-shaped metal clip (e.g., of nitinol), which is held open in the instrument jaws (see FIG. 39 of the accompanying drawings). Once the operator is satisfied with depth and orientation of the grasped leaflet, the C clip can be deployed by any of various means. For example, the free ends of the C clip can be constrained by two separate sutures that run the length of the instrument shaft. At the proximal end, the sutures can be cut to release the C clip, which will want to resiliently return toward a pre-shaped form having both ends of the C in close proximity to clamp the tissue. Another means of releasing the clip involves pivoting out a restraining lever that holds both ends of the C clamp on the respective proximal and distal surfaces of the instrument jaws.

With any of the above-described methods of attaching the suture to the desired location on the leaflet, adjustment of suture length can be made when the heart is beating. When the optimum suture length has been achieved, the suture is tied outside of the heart (i.e., to the heart wall at or near the original instrument entry point), thus preventing the leaflet from prolapsing and/or achieving improved coaptation of the leaflets.

With reference to the accompanying drawings, the following are additional improvements to what has previously been known for this general type of technology.

(A) Integration of Technology into One Compact Device

In accordance with the present invention, all or at least most of the required features and technologies are integrated into one compact, preferably disposable, hand-held, preferably articulating instrument 10. This includes the suture 130 (e.g., of GORE-TEX®), the leaflet capture detection display 60, display power 128 and light sources 62, needle 140, access site seal 50, and ports for ancillary devices and accessories such as 14, 80, 82, etc.

(B) Detection of Leaflet Capture

The jaw surfaces 40 are located at or near the distal end of instrument 10. This jaw structure captures valve leaflet tissue 16 between its two surfaces. On the proximal jaw surface, several longitudinal, spring-loaded pins 90 can be placed around the perimeter of the jaw structure (or in other locations and desired patterns as depicted). When the spring-loaded pins are in a relaxed state, an electric circuit (e.g., FIG. 21) will close (connect), thus lighting corresponding red lights 62a (indicating no tissue is present between the jaws). Once tissue is present between the jaws, the pins are depressed in the proximal direction by the tissue. The pins may operate independently of each other, thus providing an indication of orientation, partial capture, and depth of capture on the unit's display. The proximal depression of any pin causes that pin's red light circuit to open, thus turning that pin's red light off. At the same time, this causes a new circuit to close (connect), thus lighting a corresponding white light (or green light) 62b to indicate leaflet capture at the location of the associated pin. Once the tissue is captured at the locations of a sufficient number of pins having an acceptable pattern, the needle 140 can be advanced to puncture the leaflet to deploy and draw the looped suture.

Other alternative methods of leaflet capture detection are also possible. Examples include electronic detection, chemical detection, thermal detection, or other mechanical detection means. All preferably lead to indication of whether the leaflet is captured with indication of depth or orientation to determine satisfactory capture results. In particular, all detect the presence or absence of leaflet material at various points between jaw surfaces 40a and 40b, and all provide a proximal display (e.g., like 60) on handle 20. Thus (for example), in any of FIGS. 11 and 18-20, elements 90, instead of being the distal ends of pins, can be any other type of sensors (such as electronic sensors, chemical sensors, thermal sensors, other mechanical detection means, or the like), and these sensors can communicate what they detect to a display like 60 on handle 20.

(C) Detection Display

A display 60 can be integrated into the device's handle 20. This display preferably includes lights 62 capable of lighting in at least two different colors to indicate to the operator the state of tissue engagement at the jaws. Alternatively, the indication of leaflet capture can be communicated to the operator by other means or technologies (e.g., meter indicators or audible sounds to convey the state of tissue engagement with the device's jaws). The display can be designed so that it can be rotated (e.g., up to 360 degrees) about the longitudinal axis of instrument 10. In this way the display can be always in the view of the operator as he or she rotates and manipulates the instrument to facilitate capturing a leaflet.

(D) Access Site Seal

A purse-string suture is typically used around the small incision at the heart apex access site to provide a seal and eventually for incision closure after the instrument has been permanently removed. Another feature on the instrument can provide added assurance of no blood leakage during the procedure. A spring-loaded and sliding, donut-shaped, rubber grommet or small, inflatable, donut-shaped balloon 50 mounted on the instrument shaft 30 can accomplish this. Such a grommet can be mounted on a compressible spring 52 in a sliding fashion, such that when the shaft enters the heart, the grommet stops at the access site, thereby applying pressure while under spring compression and providing added assurance.

(E) Ergonomic Handle

The instrument can incorporate an ergonomic handle 20 that includes a depressable and lockable lever 20b. The locking feature can facilitate keeping the tissue captured and locked without the need for the user to maintain pressure on the device's lever. Alternatively, the instrument jaws 40 can be designed to normally be in a closed position, with depression of the lever causing the jaw surfaces to open and spread apart in preparation for leaflet capture.

(F) Ancillary Devices Port

The instrument's telescoping shafts 30*a*/30*c* (or other separate channels) can include a port to facilitate the introduction of ancillary devices from the proximal end of the device to the distal end (beyond the jaw tip). Typically, such ancillary devices can be guide wires 14, inflatable balloons 80, expandable wire baskets 82, or other appropriate devices for the purpose of momentarily stabilizing leaflet motion to facilitate capture.

(G) Leaflet Stabilization Feature

A guide wire 14 can be introduced through the ancillary device port and advanced to exit beyond the instrument jaws 40. An inflatable balloon 80 or expandable braided wire mesh basket 82 can be advanced over the wire to be deployed beyond the instrument jaws in order to stabilize the coapting leaflets in preparation for capture of one of those leaflets by the instrument jaws. Alternatively, the port (channel) can be used to inject contrast/saline solution to facilitate valve function visualization under fluoroscopy (e.g., before and/or after suture attachment).

It will be understood that the foregoing is only illustrative of the principles of the invention, and that various modifications can be made by those skilled in the art without departing from the scope and spirit of the invention. For example, the handle portion 20 of an instrument 10 in accordance with the invention can have any of many different shapes.

The invention claimed is:

1. Apparatus for attaching a tether between a leaflet of a patient's heart valve and another portion of the patient's heart, comprising:

an elongated shaft having a longitudinal axis, a proximal end and a distal end;

first and second jaw elements on the shaft, the first jaw element having a first jaw surface and the second jaw element having a second jaw surface, the jaw elements being movable relative to one another along the longitudinal axis between an open condition to admit tissue of the leaflet between the jaw surfaces and a closed condition to releasably clamp the tissue between the jaw surfaces, the jaw elements being biased to the closed condition;

a sensor including at least one sensor element on the first jaw surface and an electrical circuit, the sensor element having a first position and the electrical circuit having a first circuit condition in the absence of tissue between the jaw surfaces when the jaw elements are in the closed condition, and the sensor element having a second position and the electrical circuit having a second circuit condition in the presence of tissue between the jaw surfaces when the jaw elements are in the closed condition;

a handle attached to a proximal portion of the shaft;

a display integrated into the handle and indicating an area between the jaw surfaces occupied by the tissue; and a leaflet stabilization structure deployable from the shaft distal of the first and second jaw elements for at least partly restraining movement of the leaflet, at least one of the jaw surfaces facing away from the leaflet stabilization structure when the leaflet stabilization structure is in a deployed condition.

2. The apparatus as claimed in claim 1, wherein the leaflet stabilization structure includes a resiliently expandable wire mesh structure.

3. The apparatus as claimed in claim 1, wherein the leaflet stabilization structure includes an inflatable balloon.

4. The apparatus as claimed in claim 1, wherein the shaft includes a lumen extending along the longitudinal axis of the shaft from the proximal end to the distal end, the apparatus further comprising a control mechanism disposed in the lumen and operable to control deployment of the leaflet stabilization structure.

5. The apparatus as claimed in claim 4, wherein the control mechanism is operable to control retraction of the leaflet stabilization structure.

6. The apparatus as claimed in claim 1, wherein the leaflet stabilization structure is deployable from an aperture in the distal end of the shaft.

7. The apparatus as claimed in claim 6, wherein the shaft includes a lumen extending along the longitudinal axis of the shaft from the proximal end to the distal end, and the aperture is the distal end of the lumen.

8. The apparatus as claimed in claim 1, wherein the sensor includes at least one pin extending from the first jaw surface and at least one recess in the second jaw surface opposite the at least one pin, the at least one pin having a free end, an extended condition in which the free end extends from the first jaw surface by a first distance, and a recessed condition in which the free end extends from the first jaw surface by less than the first distance, the at least one pin being in the extended condition in the absence of tissue between the jaw surfaces when the jaw elements are in the closed condition and being in the recessed condition in the presence of tissue between the jaw surfaces when the jaw elements are in the closed condition.

9. The apparatus as claimed in claim 8, wherein the electrical circuit is in the first circuit condition when the at least one pin is in the extended condition, and the electrical circuit is in the second circuit condition when the at least one pin is in the recessed condition.

10. The apparatus as claimed in claim 1, wherein the electrical circuit changes from the first circuit condition to the second circuit condition upon movement of the first jaw element toward the second jaw element.

* * * * *